US012797037B2

(12) United States Patent
Noguchi

(10) Patent No.: US 12,797,037 B2
(45) Date of Patent: Nov. 17, 2026

(54) ULTRASOUND DIAGNOSTIC APPARATUS AND CONTROL METHOD FOR ULTRASOUND DIAGNOSTIC APPARATUS

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 156 days.

(21) Appl. No.: 18/474,153

(22) Filed: Sep. 25, 2023

(65) Prior Publication Data

US 2024/0099688 A1 Mar. 28, 2024

(30) Foreign Application Priority Data

Sep. 28, 2022 (JP) ................................. 2022-154712

(51) Int. Cl.
*A61B 8/08* (2006.01)
*A61B 8/00* (2006.01)
*A61B 34/10* (2016.01)

(52) U.S. Cl.
CPC ............ *A61B 8/0891* (2013.01); *A61B 8/085* (2013.01); *A61B 8/466* (2013.01); *A61B 8/483* (2013.01);

(Continued)

(58) Field of Classification Search
CPC ....... A61B 8/0891; A61B 8/085; A61B 8/466; A61B 8/483; A61B 8/5207; A61B 8/5223;

(Continued)

(56) References Cited

U.S. PATENT DOCUMENTS 5,329,929 A * 7/1994 Sato ......................... A61B 8/06 600/455
5,782,768 A * 7/1998 Hashimoto ............. A61B 8/14 600/443

(Continued)

FOREIGN PATENT DOCUMENTS

EP 4 000 531 A1 5/2022
JP 2014-217745 A 11/2014

(Continued)

OTHER PUBLICATIONS

The extended European search report issued by the European Patent Office on Jan. 24, 2024, which corresponds to European Patent Application No. 23200190.9-1126 and is related to U.S. Appl. No. 18/474,153.

(Continued)

*Primary Examiner* — Bo Joseph Peng
(74) *Attorney, Agent, or Firm* — Studebaker Brackett PLLC

(57) ABSTRACT

Provided are a control method for an ultrasound diagnostic apparatus and an ultrasound diagnostic apparatus capable of easily selecting a puncture position in a blood vessel.
An ultrasound diagnostic apparatus includes: a probe position detection unit that detects a position of an ultrasound probe; an image acquisition unit that acquires an ultrasound image; a monitor; a three-dimensional data generation unit that generates three-dimensional ultrasound data of a blood vessel of a subject based on a plurality of frames of the ultrasound images acquired while performing scanning with the ultrasound probe along a major axis direction of the blood vessel and the position of the ultrasound probe; a blood vessel detection unit that detects the blood vessel from the three-dimensional ultrasound data; a depth detection unit that detects a depth of the detected blood vessel; and a blood vessel image generation unit that generates a blood vessel (Continued)

image based on the position of the ultrasound probe, the detected blood vessel, and the detected depth, and that displays the blood vessel image on the monitor.

15 Claims, 18 Drawing Sheets

(52) U.S. Cl.
CPC .......... *A61B 8/5207* (2013.01); *A61B 8/5223* (2013.01); *A61B 8/5238* (2013.01); *A61B 8/5246* (2013.01); *A61B 34/10* (2016.02); *A61B 2034/107* (2016.02)

(58) Field of Classification Search
CPC ..... A61B 8/5238; A61B 8/5246; A61B 34/10; A61B 2034/107; A61B 5/0077; A61B 5/064; A61B 5/1075; A61B 5/0037; A61B 5/004; A61B 2576/02; A61B 5/0035; A61B 5/489; A61B 8/06; A61B 8/4263; A61B 8/488; A61B 8/5253
See application file for complete search history.

(56) References Cited

U.S. PATENT DOCUMENTS

| | | | | |
|---|---|---|---|---|
| 2002/0095087 | A1* | 7/2002 | Mourad | A61B 8/0816 600/442 |
| 2006/0184029 | A1* | 8/2006 | Haim | A61B 8/0833 600/443 |
| 2008/0125651 | A1 | 5/2008 | Watanabe et al. | |
| 2009/0137907 | A1* | 5/2009 | Takimoto | A61B 34/20 600/461 |
| 2009/0163809 | A1 | 6/2009 | Kane et al. | |
| 2014/0039316 | A1* | 2/2014 | Ichioka | A61B 8/13 600/443 |
| 2014/0303499 | A1 | 10/2014 | Toma et al. | |
| 2014/0350350 | A1* | 11/2014 | Imagawa | A61B 6/487 600/300 |
| 2015/0209113 | A1 | 7/2015 | Burkholz et al. | |
| 2016/0367221 | A1* | 12/2016 | Igarashi | A61B 8/5207 |
| 2016/0374644 | A1* | 12/2016 | Mauldin, Jr. | A61B 8/085 600/424 |
| 2017/0055843 | A1* | 3/2017 | Umezawa | A61B 5/0091 |
| 2018/0158201 | A1 | 6/2018 | Thompson et al. | |
| 2019/0096140 | A1 | 3/2019 | Canfield et al. | |
| 2019/0287228 | A1* | 9/2019 | Sekiguchi | G06T 7/0012 |
| 2019/0328317 | A1 | 10/2019 | Mochizuki et al. | |
| 2021/0030486 | A1* | 2/2021 | Zhang | A61B 34/20 |
| 2021/0045710 | A1* | 2/2021 | Bedi | A61B 8/12 |
| 2022/0175344 | A1 | 6/2022 | Matsumoto | |
| 2023/0233175 | A1 | 7/2023 | Matsumoto | |
| 2026/0165675 | A1 | 6/2026 | Matsumoto | |

FOREIGN PATENT DOCUMENTS

| | | | |
|---|---|---|---|
| JP | 2014-221175 | A | 11/2014 |
| JP | 2017-509372 | A | 4/2017 |
| JP | 2017-514594 | A | 6/2017 |
| JP | 2019-076748 | A | 5/2019 |
| JP | 2019-188005 | A | 10/2019 |
| WO | 2005/002446 | A1 | 1/2005 |
| WO | 2020/044770 | A1 | 3/2020 |
| WO | 2021/033446 | A1 | 2/2021 |

OTHER PUBLICATIONS

"Notice of Reasons for Refusal" Office Action issued in JP 2022-154712; mailed by the Japanese Patent Office on Jul. 21, 2026.

* cited by examiner

ULTRASOUND DIAGNOSTIC APPARATUS AND CONTROL METHOD FOR ULTRASOUND DIAGNOSTIC APPARATUS

CROSS-REFERENCE TO RELATED APPLICATIONS

The present application claims priority under 35 U.S.C. § 119 to Japanese Patent Application No. 2022-154712, filed on Sep. 28, 2022. The above application is hereby expressly incorporated by reference, in its entirety, into the present application.

BACKGROUND OF THE INVENTION

1. Field of the Invention

The present invention relates to an ultrasound diagnostic apparatus and a control method for an ultrasound diagnostic apparatus that are used to observe a blood vessel.

2. Description of the Related Art

Conventionally, dialysis, which is a treatment for artificially removing an unnecessary substance in a blood vessel of a subject, has been performed instead of kidneys. In dialysis, since an upper limb of the subject undergoes frequent punctures with a thick needle, various changes, such as stenosis, occlusion, or tortuous flow of the blood vessel, often occur in the blood vessel of the subject. In a case where various changes have occurred in the blood vessel of the subject, a puncture position in the blood vessel may not be easily selected. Therefore, normally, a so-called shunt map that records a position and a state of a blood vessel is created, and puncture is performed while confirming the created shunt map, in many cases. Since an operator often creates the shunt map by hand, the accuracy and the comprehensiveness of information in the shunt map depend on the operator's proficiency level, and creating the shunt map requires a significant amount of time.

Here, in order to easily select the puncture position in the blood vessel regardless of the operator's proficiency level, for example, a technology for automatically acquiring the position of the blood vessel of the subject imaged by a so-called ultrasound diagnostic apparatus, as disclosed in JP2014-221175A, JP2014-217745A, and JP2019-076748A, has been developed. JP2014-221175A, JP2014-217745A, and JP2019-076748A disclose a technology for acquiring a position of a blood vessel in a subject by capturing an ultrasound image while capturing an optical image of the subject and the ultrasound probe. JP2014-221175A and JP2019-076748A further disclose a technology for superimposing and displaying the ultrasound image including the blood vessel on the optical image in which the subject is captured.

SUMMARY OF THE INVENTION

Meanwhile, in a blood vessel of a subject undergoing a dialysis treatment, not only changes in a position and a shape in a plan view but also changes in a position and a shape in a depth direction often occur. In JP2014-221175A, JP2014-217745A, and JP2019-076748A, since the position and the shape of the blood vessel in the depth direction are not considered, the operator may not be able to easily select the puncture position in the blood vessel even in a case where these technologies are used.

The present invention has been made in order to solve such a conventional problem, and an object of the present invention is to provide an ultrasound diagnostic apparatus and a control method for an ultrasound diagnostic apparatus capable of easily selecting a puncture position in a blood vessel.

According to the following configuration, the above-described object can be achieved.

[1] An ultrasound diagnostic apparatus comprising:
- an ultrasound probe;
- a probe position detection unit configured to detect a position of the ultrasound probe;
- an image acquisition unit configured to acquire an ultrasound image of a subject using the ultrasound probe;
- a monitor;
- a three-dimensional data generation unit configured to generate three-dimensional ultrasound data of a blood vessel of the subject based on a plurality of frames of the ultrasound images acquired by the image acquisition unit while performing scanning with the ultrasound probe along a major axis direction of the blood vessel and the position of the ultrasound probe detected by the probe position detection unit;
- a blood vessel detection unit configured to detect the blood vessel from the three-dimensional ultrasound data generated by the three-dimensional data generation unit;
- a depth detection unit configured to detect a depth from a body surface to the blood vessel of the subject based on the blood vessel detected by the blood vessel detection unit; and
- a blood vessel image generation unit configured to generate a blood vessel image depicting the blood vessel within the subject based on the position of the ultrasound probe detected by the probe position detection unit, the blood vessel detected by the blood vessel detection unit, and the depth detected by the depth detection unit, and to display the blood vessel image on the monitor.

[2] The ultrasound diagnostic apparatus according to [1], further comprising:
- an optical camera configured to image the ultrasound probe during scanning and the subject,
- in which the blood vessel image generated by the blood vessel image generation unit is superimposed on an optical image captured by the optical camera and is displayed on the monitor.

[3] The ultrasound diagnostic apparatus according to [2],
- in which the probe position detection unit is configured to detect the position of the ultrasound probe based on the optical image captured by the optical camera.

[4] The ultrasound diagnostic apparatus according to any one of [1] to [3],
- in which the blood vessel detection unit is configured to detect a blood vessel wall and a blood vessel lumen.

[5] The ultrasound diagnostic apparatus according to [4], further comprising:
- a blood vessel size calculation unit configured to calculate a thickness of the blood vessel wall or a diameter of the blood vessel lumen based on the blood vessel wall and the blood vessel lumen detected by the blood vessel detection unit.

[6] The ultrasound diagnostic apparatus according to [5], further comprising:

a first abnormal location detection unit configured to detect a location where a spatial change rate of the thickness of the blood vessel wall or the diameter of the blood vessel lumen calculated by the blood vessel size calculation unit exceeds a predetermined change rate threshold value, and to display the location on the monitor.

[7] The ultrasound diagnostic apparatus according to any one of [4] to [6], in which the three-dimensional data generation unit is configured to acquire a B-mode image and a Doppler image, and the blood vessel detection unit is configured to detect the blood vessel lumen based on the B-mode image and the Doppler image.

[8] The ultrasound diagnostic apparatus according to any one of [1] to [7], in which the blood vessel image generation unit is configured to change a display form of the blood vessel image on the monitor according to the depth detected by the depth detection unit.

[9] The ultrasound diagnostic apparatus according to any one of [1] to [8], further comprising:

a three-dimensional image generation unit configured to generate a three-dimensional ultrasound image corresponding to any location designated by a user for the blood vessel image from the three-dimensional ultrasound data generated by the three-dimensional data generation unit, and to display the three-dimensional ultrasound image on the monitor.

[10] The ultrasound diagnostic apparatus according to any one of [1] to [9], further comprising:

a recommended puncture pathway calculation unit configured to calculate a recommended puncture pathway including a recommended puncture direction and a recommended puncture angle with respect to the body surface at a puncture location designated by a user for the blood vessel image from the three-dimensional ultrasound data generated by the three-dimensional data generation unit, and to display the recommended puncture pathway on the monitor.

[11] The ultrasound diagnostic apparatus according to any one of [1] to [10], further comprising:

a blood vessel determination unit configured to determine whether the blood vessel detected by the blood vessel detection unit is an artery or a vein, in which the blood vessel image generation unit is configured to generate the blood vessel image in which a depiction form of the blood vessel is changed according to a determination result by the blood vessel determination unit.

[12] The ultrasound diagnostic apparatus according to any one of [1] to [11], further comprising:

a nerve bundle detection unit configured to detect a nerve bundle from the three-dimensional ultrasound data generated by the three-dimensional data generation unit, and to display the nerve bundle on the monitor.

[13] The ultrasound diagnostic apparatus according to [4], further comprising:

an association unit configured to associate positions of a past blood vessel image and of a current blood vessel image with each other; and a finding location display unit configured to superimpose, on the current blood vessel image, a current location associated with a past finding location on the past blood vessel image by the association unit, and to display the current location on the monitor.

[14] The ultrasound diagnostic apparatus according to [13], further comprising:

a past image display unit configured to display a past finding content and a past ultrasound image corresponding to the current location, which is displayed on the monitor by the finding location display unit and designated by a user, on the monitor.

[15] The ultrasound diagnostic apparatus according to [14], further comprising:

a similar image display unit configured to search a plurality of frames of the ultrasound images acquired in a current examination for an ultrasound image similar to the past ultrasound image, and to display the ultrasound image on the monitor.

[16] The ultrasound diagnostic apparatus according to any one of to [15], further comprising:

a blood vessel size calculation unit configured to calculate a diameter of the blood vessel lumen based on the blood vessel lumen detected by the blood vessel detection unit; and a second abnormal location detection unit configured to detect a location where a difference between a diameter of the blood vessel lumen in the past blood vessel image and a diameter of the blood vessel lumen in the current blood vessel image, which are calculated by the blood vessel size calculation unit, exceeds a predetermined lumen diameter threshold value, and to display the location on the monitor.

[17] A control method for an ultrasound diagnostic apparatus, comprising:

detecting a position of an ultrasound probe;

acquiring an ultrasound image of a subject using the ultrasound probe;

generating three-dimensional ultrasound data of a blood vessel of the subject based on a plurality of frames of the ultrasound images acquired while performing scanning with the ultrasound probe along a major axis direction of the blood vessel and the detected position of the ultrasound probe;

detecting the blood vessel from the generated three-dimensional ultrasound data;

detecting a depth from a body surface to the blood vessel of the subject based on the detected blood vessel; and generating a blood vessel image depicting the blood vessel within the subject based on the detected position of the ultrasound probe, the detected blood vessel, and the detected depth, and displaying the blood vessel image on a monitor.

In the present invention, an ultrasound diagnostic apparatus comprises: an ultrasound probe; a probe position detection unit configured to detect a position of the ultrasound probe; an image acquisition unit configured to acquire an ultrasound image of a subject using the ultrasound probe; a monitor; a three-dimensional data generation unit configured to generate three-dimensional ultrasound data of a blood vessel of the subject based on a plurality of frames of the ultrasound images acquired by the image acquisition unit while performing scanning with the ultrasound probe along a major axis direction of the blood vessel and the position of the ultrasound probe detected by the probe position detection unit; a blood vessel detection unit configured to detect the blood vessel from the three-dimensional ultrasound data generated by the three-dimensional data generation unit; a depth detection unit configured to detect a depth from a body surface to the blood vessel of the subject based on the blood vessel detected by the blood vessel detection unit; and a blood vessel image generation unit configured to generate a blood vessel image depicting the blood vessel within the subject based on the position of the ultrasound probe detected by the probe position detection unit, the blood vessel detected by the blood vessel detection unit, and the depth detected by the depth detection unit, and to display the blood vessel image on the monitor. Therefore, the user can easily select the puncture position in the blood vessel.

DESCRIPTION OF THE PREFERRED EMBODIMENTS

Hereinafter, embodiments of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Embodiment 1

Figure 1:
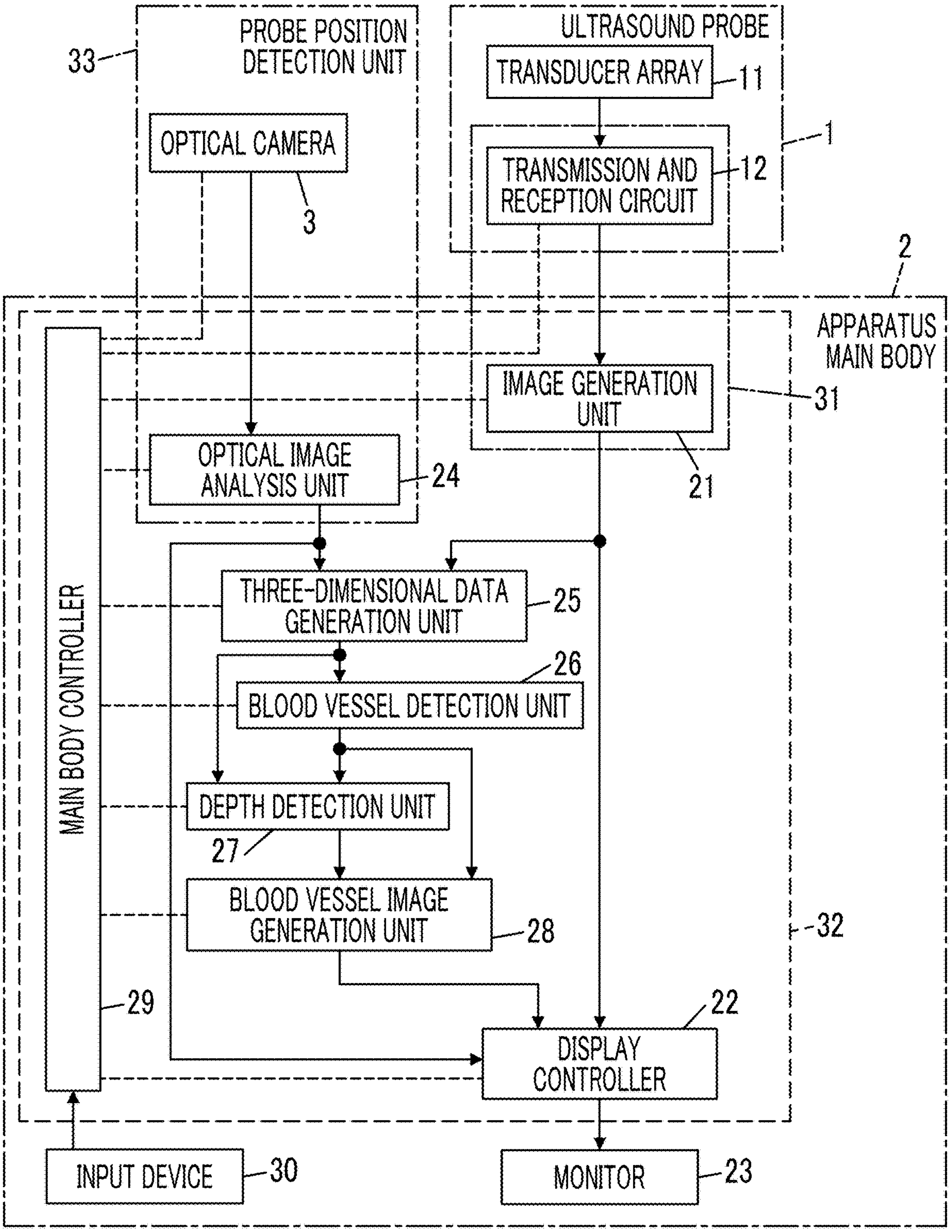
FIG. 1 is a block diagram showing a configuration of an ultrasound diagnostic apparatus according to Embodiment 1 of the present invention.

FIG. 1 shows a configuration of an ultrasound diagnostic apparatus according to Embodiment 1 of the present invention. The ultrasound diagnostic apparatus comprises an ultrasound probe 1, an apparatus main body 2 connected to the ultrasound probe 1, and an optical camera 3. The ultrasound diagnostic apparatus is used to observe a blood vessel of a subject.

The ultrasound probe 1 includes a transducer array 11. A transmission and reception circuit 12 is connected to the transducer array 11.

The apparatus main body 2 includes an image generation unit 21 connected to the transmission and reception circuit 12 of the ultrasound probe 1. A display controller 22 and a monitor 23 are sequentially connected to the image generation unit 21. The apparatus main body 2 comprises an optical image analysis unit 24 connected to the optical camera 3. A three-dimensional data generation unit 25 is connected to the image generation unit 21 and the optical image analysis unit 24. A blood vessel detection unit 26 is connected to the three-dimensional data generation unit 25. A depth detection unit 27 is connected to the three-dimensional data generation unit 25 and the blood vessel detection unit 26. A blood vessel image generation unit 28 is connected to the blood vessel detection unit 26 and the depth detection unit 27. The optical image analysis unit 24 and the blood vessel image generation unit 28 are connected to the display controller 22. In addition, a main body controller 29 is connected to the optical camera 3, the transmission and reception circuit 12, the image generation unit 21, the display controller 22, the optical image analysis unit 24, the three-dimensional data generation unit 25, the blood vessel detection unit 26, the depth detection unit 27, and the blood vessel image generation unit 28. An input device 30 is connected to the main body controller 29.

In addition, the transmission and reception circuit 12 and the image generation unit 21 constitute an image acquisition unit 31. In addition, the image generation unit 21, the display controller 22, the optical image analysis unit 24, the three-dimensional data generation unit 25, the blood vessel detection unit 26, the depth detection unit 27, the blood vessel image generation unit 28, and the main body controller 29 constitute a processor 32 for the apparatus main body 2. Further, the optical camera 3 and the optical image analysis unit 24 constitute a probe position detection unit 33.

The transducer array 11 of the ultrasound probe 1 includes a plurality of ultrasound transducers one-dimensionally or two-dimensionally arranged. Each of these ultrasound transducers transmits an ultrasound wave in accordance with a drive signal supplied from the transmission and reception circuit 12 and receives an ultrasound echo from a subject to output a signal based on the ultrasound echo. For example, each ultrasound transducer is composed of a piezoelectric body consisting of a piezoelectric ceramic represented by lead zirconate titanate (PZT), a polymer piezoelectric element represented by poly vinylidene di fluoride (PVDF), a piezoelectric single crystal represented by lead magnesium niobate-lead titanate (PMN-PT), or the like, and electrodes formed at both ends of the piezoelectric body.

Figure 2:
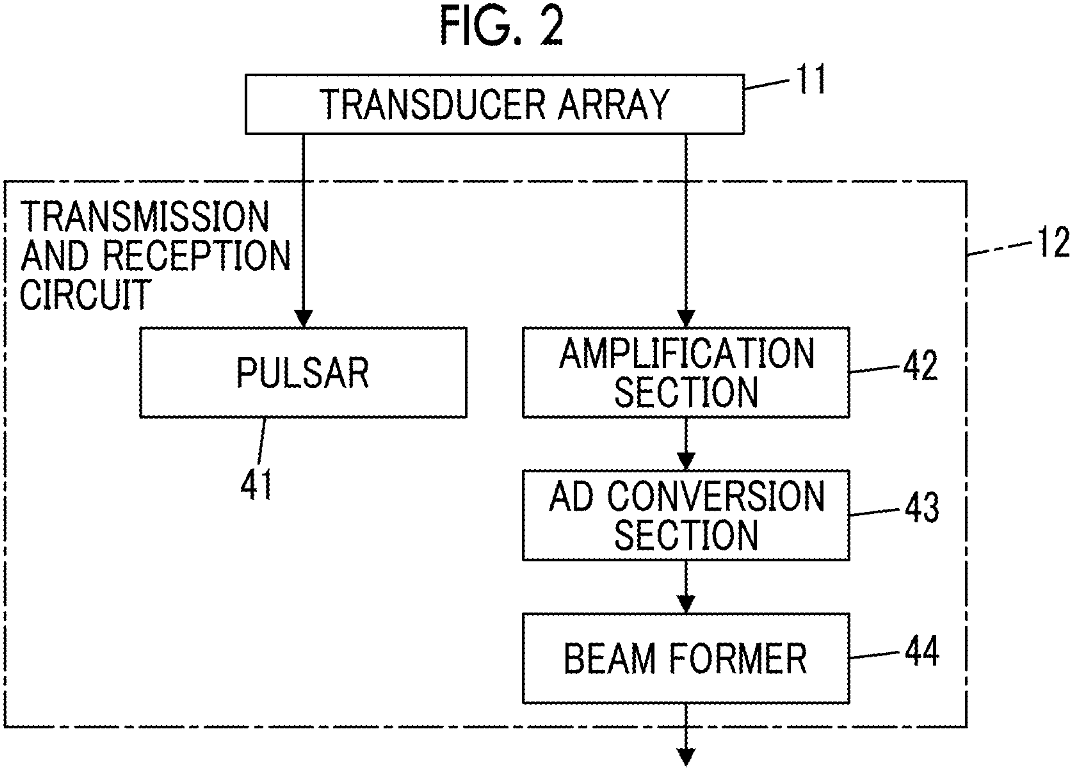
FIG. 2 is a block diagram showing a configuration of a transmission and reception circuit in Embodiment 1 of the present invention.

The transmission and reception circuit 12 transmits the ultrasound wave from the transducer array 11 and generates a sound ray signal based on a reception signal acquired by the transducer array 11, under the control of the main body controller 29. As shown in FIG. 2, the transmission and reception circuit 12 includes a pulsar 41 connected to the transducer array 11, and an amplification section 42, an analog-to-digital (AD) conversion section 43, and a beam former 44 that are sequentially connected in series to the transducer array 11.

The pulsar 41 includes, for example, a plurality of pulse generators, and adjusts an amount of delay of each of drive signals and supplies the drive signals to the plurality of ultrasound transducers such that ultrasound waves transmitted from the plurality of ultrasound transducers of the transducer array 11 form an ultrasound beam based on a transmission delay pattern selected according to a control signal from the main body controller 29. In this way, in a case where a pulsed or continuous wave-like voltage is applied to the electrodes of the ultrasound transducer of the transducer array 11, the piezoelectric body expands and contracts to generate a pulsed or continuous wave-like ultrasound wave from each of the ultrasound transducers, whereby an ultrasound beam is formed from the combined wave of these ultrasound waves.

The transmitted ultrasound beam is reflected in, for example, a target such as a site of the subject and propagates toward the transducer array 11 of the ultrasound probe 1. The ultrasound echo propagating toward the transducer array 11 in this way is received by each of the ultrasound transducers constituting the transducer array 11. In this case, each of the ultrasound transducers constituting the transducer array 11 receives the propagating ultrasound echo to expand and contract to generate a reception signal, which is an electrical signal, and outputs these reception signals to the amplification section 42.

The amplification section 42 amplifies the signal input from each of the ultrasound transducers constituting the transducer array 11 and transmits the amplified signal to the AD conversion section 43. The AD conversion section 43 converts the signal transmitted from the amplification section 42 into digital reception data. The beam former 44 performs so-called reception focus processing by applying and adding a delay to each reception data received from the AD conversion section 43. By this reception focus processing, each reception data converted by the AD conversion section 43 is phase-added, and a sound ray signal in which the focus of the ultrasound echo is narrowed down is acquired.

Figure 3:
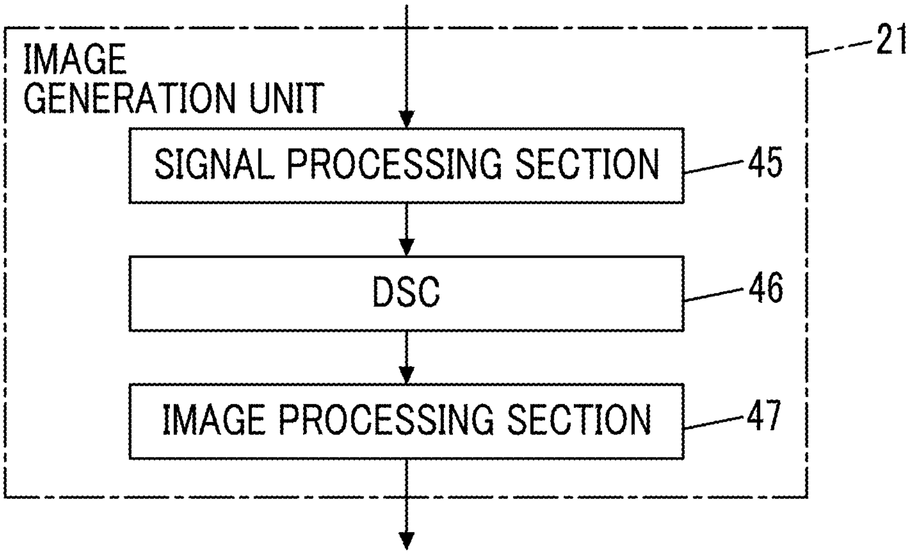
FIG. 3 is a block diagram showing a configuration of an image generation unit in Embodiment 1 of the present invention.

As shown in FIG. 3, the image generation unit 21 has a configuration in which a signal processing section 45, a digital scan converter (DSC) 46, and an image processing section 47 are sequentially connected in series.

The signal processing section 45 generates a B-mode image signal, which is tomographic image information regarding tissues within the subject, by performing, on the sound ray signal received from the transmission and reception circuit 12, correction of the attenuation due to the distance according to the depth of the reflection position of the ultrasound wave using a sound velocity value set by the main body controller 29 and then performing envelope detection processing.

The DSC 46 converts (raster-converts) the B-mode image signal generated by the signal processing section 45 into an image signal in accordance with a normal television signal scanning method.

The image processing section 47 performs various types of necessary image processing such as gradation processing on the B-mode image signal input from the DSC 46 and then sends out the B-mode image signal to the display controller 22 and the three-dimensional data generation unit 25. Hereinafter, the B-mode image signal that has been subjected to image processing by the image processing section 47 is referred to as an ultrasound image.

The display controller 22 performs predetermined processing on the ultrasound image or the like generated by the image generation unit 21 and displays the ultrasound image or the like on the monitor 23, under the control of the main body controller 29.

The monitor 23 performs various kinds of display under the control of the display controller 22. The monitor 23 can include a display device such as a liquid crystal display (LCD), or an organic electroluminescence (EL) display, for example.

The optical camera 3 includes, for example, an image sensor, such as a so-called charge coupled device (CCD) image sensor or a so-called a complementary metal-oxide-semiconductor (CMOS) image sensor, and images a body surface of the subject and the ultrasound probe 1 disposed on the body surface of the subject to acquire an optical image. The optical camera 3 sends out the acquired optical image to the optical image analysis unit 24.

The optical image analysis unit 24 detects a position of the ultrasound probe 1 on the body surface of the subject by analyzing, for example, the optical image captured by the optical camera 3. For example, in a case where a marker for detecting the position of the ultrasound probe 1, for example, a so-called augmented reality marker (AR marker) or the like, is attached to the ultrasound probe 1, the optical image analysis unit 24 can detect the position of the ultrasound probe 1 by recognizing the marker.

In addition, the optical image analysis unit 24 stores, for example, a plurality of template images representing the ultrasound probe 1 and the body surface of the subject, and can detect the ultrasound probe 1 and the body surface of the subject by searching the optical image through a template matching method using the plurality of template images and can also detect the position of the ultrasound probe 1 on the body surface of the subject. Further, the optical image analysis unit 24 includes, for example, a machine learning model that has learned a large number of optical images showing general ultrasound probes and body surfaces of subjects, and can also detect the position of the ultrasound probe 1 on the body surface of the subject by using the machine learning model.

The three-dimensional data generation unit 25 generates three-dimensional ultrasound data of the blood vessel of the subject based on a plurality of frames of the ultrasound images including a minor axis image of the blood vessel, which are acquired by the image acquisition unit 31 while performing scanning with the ultrasound probe 1 along a major axis direction of the blood vessel, that is, along a flow direction of the blood vessel, and the position of the ultrasound probe 1 detected by the probe position detection unit 33. Here, the minor axis image of the blood vessel refers to a tomographic plane perpendicular to the major axis direction of the blood vessel.

Figure 4:
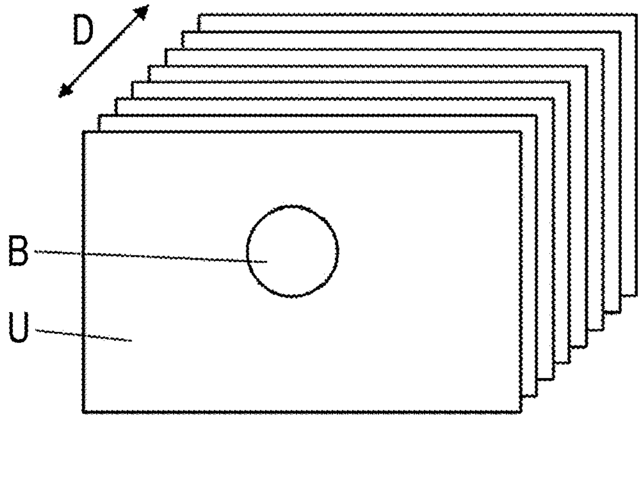
FIG. 4 is a diagram showing a plurality of frames of ultrasound images used to generate three-dimensional ultrasound data.

In this case, the three-dimensional data generation unit 25 can generate the three-dimensional ultrasound data by arranging the plurality of frames of ultrasound images U showing a blood vessel B along a major axis direction D based on the position of the ultrasound probe 1 detected by the probe position detection unit 33, as shown in FIG. 4, for example. The three-dimensional data generation unit 25 can also generate smoother continuous three-dimensional data of the blood vessel B and the surrounding tissue of the blood vessel B in the major axis direction D by analyzing the plurality of frames of the ultrasound images U and estimating and interpolating data between the plurality of frames of the ultrasound images U in the major axis direction D.

The blood vessel detection unit 26 detects the blood vessel B from the three-dimensional ultrasound data by analyzing the three-dimensional ultrasound data generated by the three-dimensional data generation unit 25. The blood vessel detection unit 26 can detect, for example, a cross-section of the blood vessel B in the three-dimensional ultrasound data through the template matching method for a cross-section perpendicular to the major axis direction D and can detect the three-dimensional blood vessel B using a set of detection results thereof. In addition, the blood vessel detection unit 26 can also detect the three-dimensional blood vessel B from the three-dimensional ultrasound data by using a machine learning model that has learned a large amount of three-dimensional ultrasound data and the three-dimensional blood vessels B present within the large amount of three-dimensional ultrasound data. Further, the blood vessel detection unit 26 can detect the blood vessel B by detecting a blood vessel wall or a blood vessel lumen. Here, the blood vessel lumen refers to a spatial region present inside the blood vessel wall.

The depth detection unit 27 detects a depth from the body surface to the blood vessel B of the subject over the entire length of the detected blood vessel B based on the blood vessel B detected by the blood vessel detection unit 26. The depth detection unit 27 can detect the depth from the body surface to the blood vessel B of the subject by measuring, over the entire length of the detected blood vessel B, a distance in a depth direction between an upper end part of the ultrasound data, that is, the body surface, and the center of the blood vessel lumen, or a shortest distance in the depth direction between the upper end part of the ultrasound data, that is, the body surface, and the blood vessel wall, in the three-dimensional ultrasound data.

Figure 5:
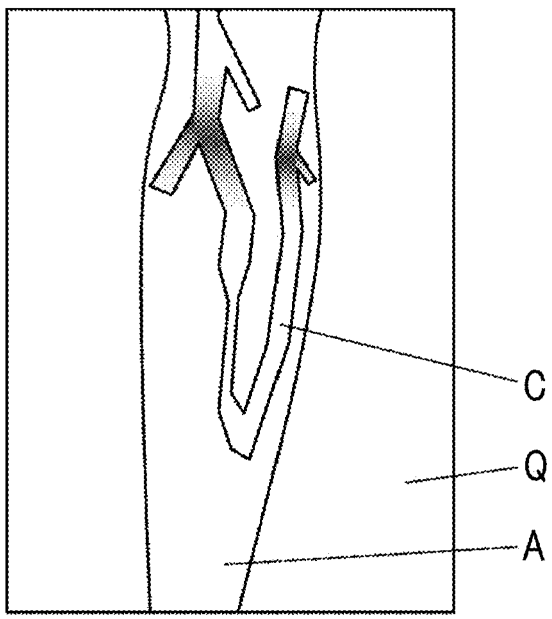
FIG. 5 is a diagram showing an example of a blood vessel image superimposed on an optical image in which an upper limb of a subject is captured.

The blood vessel image generation unit 28 generates, for example, as shown in FIG. 5, a blood vessel image C depicting the blood vessel B within the subject based on the position of the ultrasound probe 1 detected by the probe position detection unit 33, the three-dimensional blood vessel B detected by the blood vessel detection unit 26, and the depth of the blood vessel B detected by the depth detection unit 27, and superimposes the blood vessel image C on a body surface A of the subject shown in an optical image Q captured by the optical camera 3 and displays the blood vessel image C on the monitor 23. FIG. 5 shows an example in which the blood vessel image C is superimposed on the body surface A of an upper limb of the subject shown in the optical image Q.

In the blood vessel image C, a display form can be changed according to the depth of the blood vessel B, such as using, in addition to a position and a shape of the blood vessel B along a plane represented by the optical image Q, that is, in a plan view, for example, color intensity, chroma saturation, transparency, brightness, a display form of a color or a contour line, or the like to represent the depth of the blood vessel B. For example, in a case where the depth of the blood vessel B is represented by the color intensity, the blood vessel image C can represent that a location with a darker color corresponds to a deeper position of the blood vessel B, and the blood vessel image C can represent that a location with a lighter color corresponds to a shallower position of the blood vessel B. The user can easily grasp the position, the shape, and the depth of the blood vessel B by confirming the blood vessel image C shown on the monitor 23 and can easily select the puncture position in the dialysis treatment or the like.

The main body controller 29 controls each unit of the apparatus main body 2 and the ultrasound probe 1 in accordance with a program recorded in advance, or the like.

The input device 30 accepts the input operation from the examiner and sends out input information to the main body controller 29. The input device 30 is composed of, for example, a device for the examiner to perform an input operation, such as a keyboard, a mouse, a trackball, a touchpad, or a touch panel.

Although the processor 32 including the image generation unit 21, the display controller 22, the optical image analysis unit 24, the three-dimensional data generation unit 25, the blood vessel detection unit 26, the depth detection unit 27, the blood vessel image generation unit 28, and the main body controller 29 may be composed of a central processing unit (CPU) and a control program for causing the CPU to perform various types of processing, the processor 32 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the image generation unit 21, the display controller 22, the optical image analysis unit 24, the three-dimensional data generation unit 25, the blood vessel detection unit 26, the depth detection unit 27, the blood vessel image generation unit 28, and the main body controller 29 of the processor 32 can also be configured by being integrated partially or entirely into one CPU or the like.

Next, an example of the operation of the ultrasound diagnostic apparatus according to Embodiment 1 will be described using the flowchart of FIG. 6.

First, in step S1, the main body controller 29 controls each unit of the ultrasound diagnostic apparatus to start scanning of the ultrasound probe 1. In this case, the main body controller 29 can start the scanning of the ultrasound probe 1, for example, with an input of an instruction to start the scanning of the ultrasound probe 1 from the user via the input device 30, as a trigger. From then on, the user performs the scanning with the ultrasound probe 1 while moving the ultrasound probe 1 along the major axis direction D of the blood vessel B in a state in which the ultrasound probe 1 is in contact with the body surface A of the subject such that the minor axis image of the blood vessel B of the subject is captured.

Next, in step S2, the probe position detection unit 33 detects the position of the ultrasound probe 1. In this case, the optical camera 3 of the probe position detection unit 33 images the body surface A of the subject and the ultrasound probe 1 to acquire the optical image Q, and the optical image analysis unit 24 analyzes the optical image Q, whereby the position of the ultrasound probe 1 on the body surface A of the subject is detected. In a case where a marker for detecting the position of the ultrasound probe 1 is attached to the ultrasound probe 1, the optical image analysis unit 24 can detect the position of the ultrasound probe 1 by recognizing the marker. In addition, the optical image analysis unit 24 can also detect the position of the ultrasound probe 1 through a template matching method or a method using a machine learning model.

In step S3, the image acquisition unit 31 acquires the ultrasound image U. In this case, the transducer array 11 of the ultrasound probe 1 transmits the ultrasound beam into the subject and receives the ultrasound echo from the inside of the subject, thereby generating the reception signal. The transmission and reception circuit 12 of the image acquisition unit 31 performs so-called reception focus processing on the reception signal to generate the sound ray signal, under the control of the main body controller 29. The sound ray signal generated by the transmission and reception circuit 12 is sent out to the image generation unit 21. The image generation unit 21 generates the ultrasound image U using the sound ray signal sent out from the transmission and reception circuit 12.

Here, since the processing of steps S2 and S3 is performed substantially at the same time, the position of the ultrasound probe 1 detected in step S2 and the position of the ultrasound probe 1 in a case where the ultrasound image U is acquired in step S3 can be regarded as the same.

In step S4, the main body controller 29 determines whether or not to end the scanning of the ultrasound probe 1. The main body controller 29 can determine to end the scanning of the ultrasound probe 1, for example, in a case where an instruction to end the scanning of the ultrasound probe 1 is input by the user via the input device 30. The main body controller 29 can determine to continue the scanning of the ultrasound probe 1, for example, in a case where an instruction to end the scanning of the ultrasound probe 1 is not input by the user via the input device 30.

In a case where it is determined in step S4 to continue the scanning of the ultrasound probe 1, the process returns to step S2, and the position of the ultrasound probe 1 is newly detected. In subsequent step S3, the ultrasound image U is newly acquired, and the process proceeds to step S4. In this way, processing of steps S2 to S4 is repeated as long as it is determined in step S4 to continue the scanning of the ultrasound probe 1. In a case where it is determined in step S4 to end the scanning of the ultrasound probe 1, the process proceeds to step S5.

In step S5, the three-dimensional data generation unit 25 generates the three-dimensional ultrasound data of the blood vessel B based on the position of the ultrasound probe 1 detected in the repetition of steps S2 to S4 and the plurality of continuous frames of the ultrasound images U acquired in the repetition of steps S2 to S4. For example, as shown in FIG. 4, the three-dimensional data generation unit 25 can generate the three-dimensional ultrasound data by arranging the plurality of frames of the ultrasound images U acquired in step S3 along the major axis direction D based on the position of the ultrasound probe 1 detected in step S2.

In step S6, the blood vessel detection unit 26 detects the blood vessel B from the three-dimensional ultrasound data by analyzing the three-dimensional ultrasound data generated in step S5. The blood vessel detection unit 26 can detect, for example, a cross-section of the blood vessel B in the three-dimensional ultrasound data through the template matching method for a cross-section perpendicular to the major axis direction D and can detect the three-dimensional blood vessel B using a set of detection results thereof. In addition, the blood vessel detection unit 26 can also detect the three-dimensional blood vessel B through a method using a machine learning model. In this case, the blood vessel detection unit 26 can detect the blood vessel B by detecting a blood vessel wall or a blood vessel lumen.

In step S7, the depth detection unit 27 detects the depth from the body surface A to the blood vessel B of the subject over the entire length of the detected blood vessel B based on the three-dimensional blood vessel B detected in step S6. The depth detection unit 27 can detect the depth from the body surface A to the blood vessel B of the subject by measuring, over the entire length of the detected blood vessel B, the distance in the depth direction between the upper end part of the ultrasound data, that is, the body surface A, and the center of the blood vessel lumen, or the shortest distance in the depth direction between the upper end part of the ultrasound data, that is, the body surface A, and the blood vessel wall, in the three-dimensional ultrasound data.

In step S8, the blood vessel image generation unit 28 generates, for example, as shown in FIG. 5, the blood vessel image C depicting the blood vessel B within the subject based on the position of the ultrasound probe 1 detected in step S2, the three-dimensional blood vessel B detected in step S6, and the depth of the blood vessel B detected in step S7. The blood vessel image C can represent the depth of the blood vessel B using, for example, the color intensity, in addition to the position and the shape of the blood vessel B along the plane represented by the optical image Q, that is, in a plan view. For example, the blood vessel image C can represent that a location with a darker color corresponds to a deeper position of the blood vessel B, and the blood vessel image C can represent that a location with a lighter color corresponds to a shallower position of the blood vessel B.

In step S9, the optical camera 3 acquires the optical image Q in which the body surface A of the subject is captured, under the control of the main body controller 29.

In step S10, the blood vessel image generation unit 28 superimposes the blood vessel image C generated in step S8 on, for example, as shown in FIG. 5, the body surface A of the subject captured in the optical image Q acquired in step S9 and displays the blood vessel image C on the monitor 23. In this case, the blood vessel image generation unit 28 can perform registration between, for example, the body surface A of the subject shown in the optical image Q captured in step S2 and the body surface A of the subject shown in the optical image Q captured in step S9.

The user can easily grasp the position, the shape, and the depth of the blood vessel B within the subject by confirming the blood vessel image C displayed on the monitor 23 in this manner and can easily select the puncture position in the dialysis treatment or the like.

Figure 6:
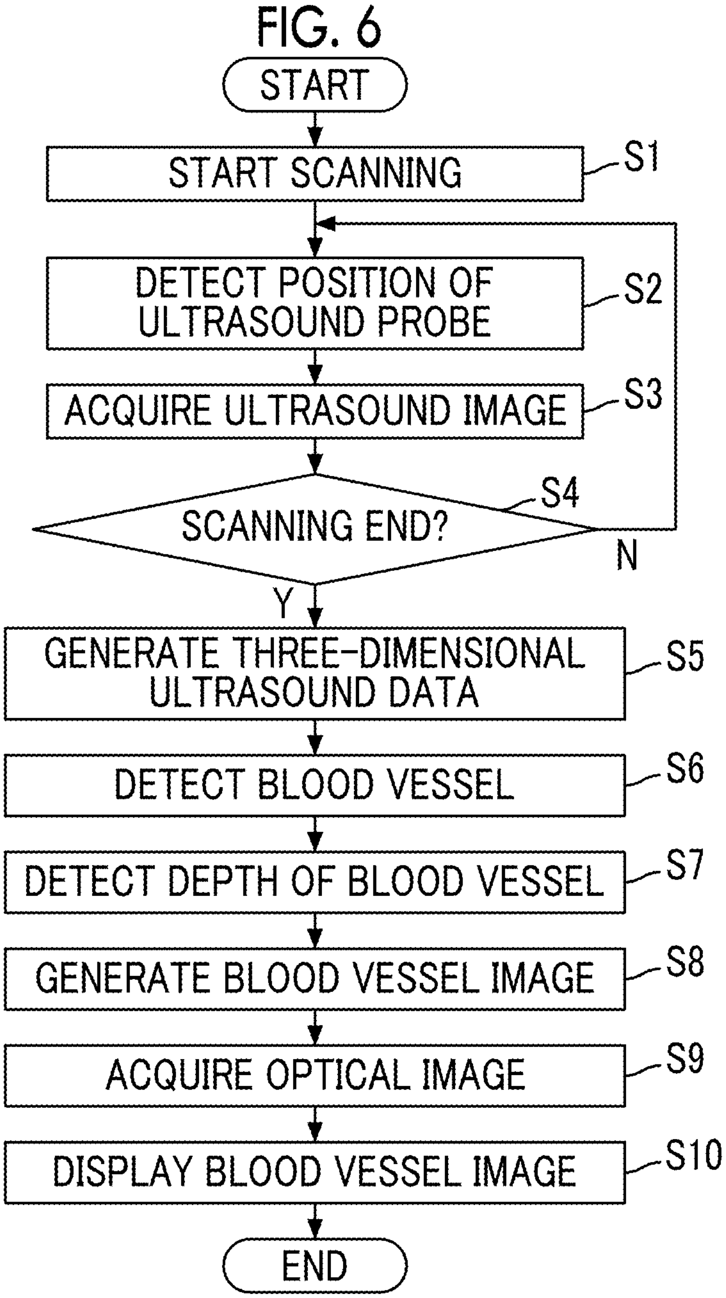
FIG. 6 is a flowchart showing an operation of the ultrasound diagnostic apparatus according to Embodiment 1 of the present invention.

In a case where the processing of step S10 is completed, the operation of the ultrasound diagnostic apparatus following the flowchart of FIG. 6 is completed.

From the above, with the ultrasound diagnostic apparatus of Embodiment 1 of the present invention, the three-dimensional data generation unit 25 generates the three-dimensional ultrasound data of the blood vessel B of the subject based on the plurality of frames of the ultrasound images U acquired by the image acquisition unit 31 while performing scanning with the ultrasound probe 1 along the major axis direction D of the blood vessel B and the position of the ultrasound probe 1 detected by the probe position detection unit 33, the blood vessel detection unit 26 detects the blood vessel B from the three-dimensional ultrasound data generated by the three-dimensional data generation unit 25, the depth detection unit 27 detects the depth from the body surface A to the blood vessel B of the subject based on the three-dimensional blood vessel B detected by the blood vessel detection unit 26, and the blood vessel image generation unit 28 generates the blood vessel image C depicting the blood vessel B within the subject based on the position of the ultrasound probe 1 detected by the probe position detection unit 33, the three-dimensional blood vessel B detected by the blood vessel detection unit 26, and the depth detected by the depth detection unit 27 and displays the blood vessel image C on the monitor 23. Therefore, the user can easily grasp the position, the shape, and the depth of the blood vessel B within the subject by confirming the blood vessel image C and can easily select the puncture position in the dialysis treatment or the like.

Although a case where the transmission and reception circuit 12 is provided in the ultrasound probe 1 has been described, the transmission and reception circuit 12 may be provided in the apparatus main body 2.

In addition, although a case where the image generation unit 21 is provided in the apparatus main body 2 has been described, the image generation unit 21 may be provided in the ultrasound probe 1.

Further, the apparatus main body 2 may be a so-called stationary type, a portable type that is easy to carry, or a so-called handheld type that is composed of, for example, a smartphone or a tablet type computer. As described above, the type of the device that constitutes the apparatus main body 2 is not particularly limited.

Figure 7:
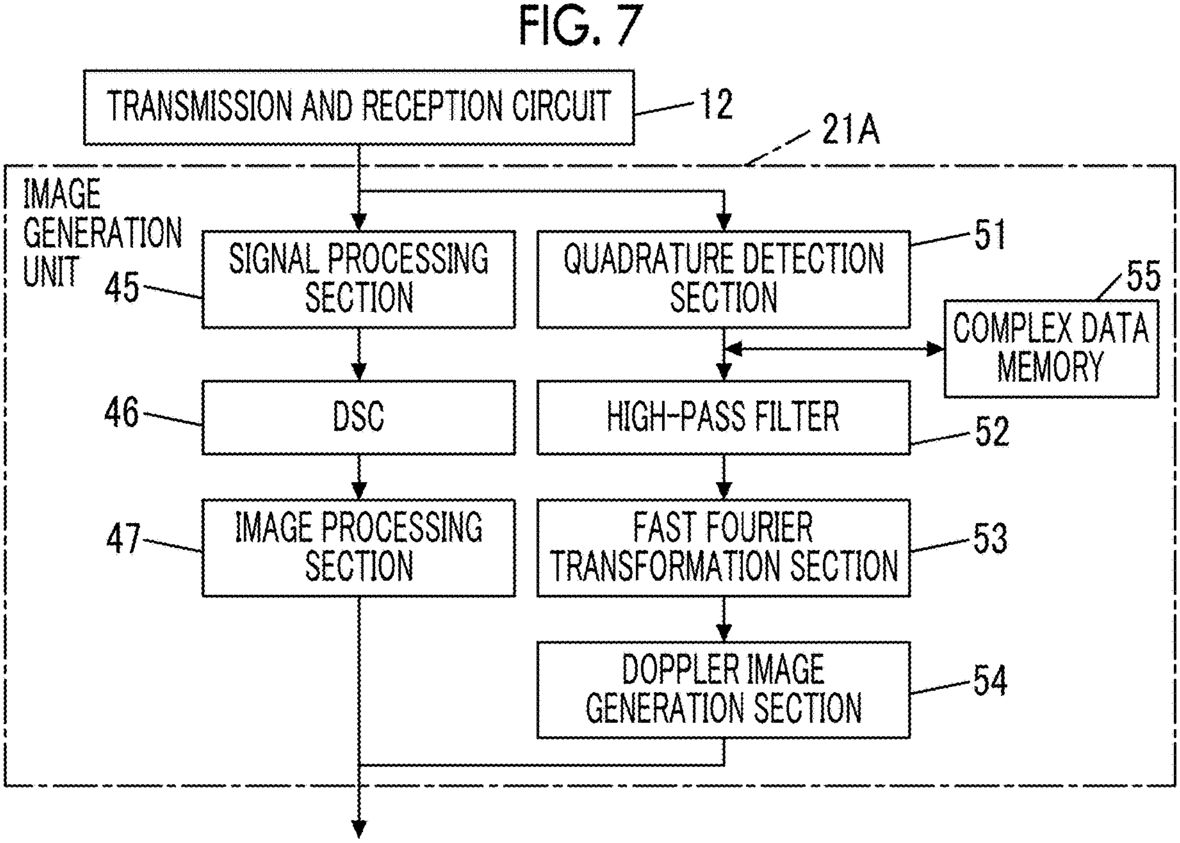
FIG. 7 is a block diagram showing a configuration of an image generation unit in a modification example of Embodiment 1.

Further, although a case where the image generation unit 21 generates the B-mode image as the ultrasound image U has been described, it is also possible to further generate a so-called Doppler image. In this case, the apparatus main body 2 can comprise, for example, an image generation unit 21A having a configuration shown in FIG. 7.

The image generation unit 21A comprises the signal processing section 45 and a quadrature detection section 51 connected to the transmission and reception circuit 12. Similar to the image generation unit 21 shown in FIG. 3, the DSC 46 and the image processing section 47 are sequentially connected to the signal processing section 45. In addition, a high-pass filter 52, a high-speed Fourier transformation section 53, and a Doppler image generation section 54 are sequentially connected to the quadrature detection section 51. Further, a complex data memory 55 is connected to the quadrature detection section 51 and the high-pass filter 52.

The quadrature detection section 51 mixes the sound ray signal generated by the transmission and reception circuit 12 with a carrier signal having a reference frequency to perform quadrature detection on the sound ray signal, thereby converting the sound ray signal into complex data.

The high-pass filter 52 functions as a so-called wall filter and removes a frequency component derived from the motion of the body tissue within the subject, from the complex data generated by the quadrature detection section 51.

The high-speed Fourier transformation section 53 performs frequency analysis by performing a Fourier transform on the complex data of a plurality of sample points, obtains the blood flow velocity, and generates a spectrum signal.

The Doppler image generation section 54 generates a Doppler image by aligning the spectrum signals generated by the high-speed Fourier transformation section 53 on a time axis and representing the magnitude of each frequency component as brightness. In the Doppler image, the lateral axis indicates a time axis, the vertical axis indicates a Doppler shift frequency, that is, a flow velocity, and the brightness of the waveform represents power in each frequency component.

The complex data memory 55 stores the complex data converted from the sound ray signal by the quadrature detection section 51.

Since the Doppler image is an image of a location where blood flow is present, the image of the blood vessel lumen can be clearly captured in the minor axis image of the blood vessel B, for example, even in a case where the blood vessel wall is thickened, a case where a plaque is generated in the blood vessel B to cause the stenosis of the blood vessel B, and the like.

The three-dimensional data generation unit 25 can acquire the B-mode image and the Doppler image, which are generated by the image generation unit 21A, and can generate the three-dimensional ultrasound data based on the plurality of continuous frames of the B-mode images and the plurality of continuous frames of the Doppler images.

The blood vessel detection unit 26 can detect the blood vessel lumen from three-dimensional ultrasound data based on the B-mode image and the Doppler image. Since the image of the blood vessel lumen is clearly captured in the Doppler image, the blood vessel detection unit 26 can improve the detection accuracy of the blood vessel lumen by detecting the blood vessel lumen based on both the B-mode image and the Doppler image, as compared with the blood vessel lumen detected based only on the B-mode image.

In a case where the blood vessel detection unit 26 detects the blood vessel lumen based on both the B-mode image and the Doppler image and the depth detection unit 27 detects the distance in the depth direction from the body surface A of the subject to the center of the blood vessel lumen as the depth of the blood vessel B, it is possible to improve the detection accuracy of the depth of the blood vessel B.

Embodiment 2

In Embodiment 1, a case where the position of the ultrasound probe 1 is detected based on the optical image Q has been described, but the detection method of the ultrasound probe 1 is not limited to this.

Figure 8:
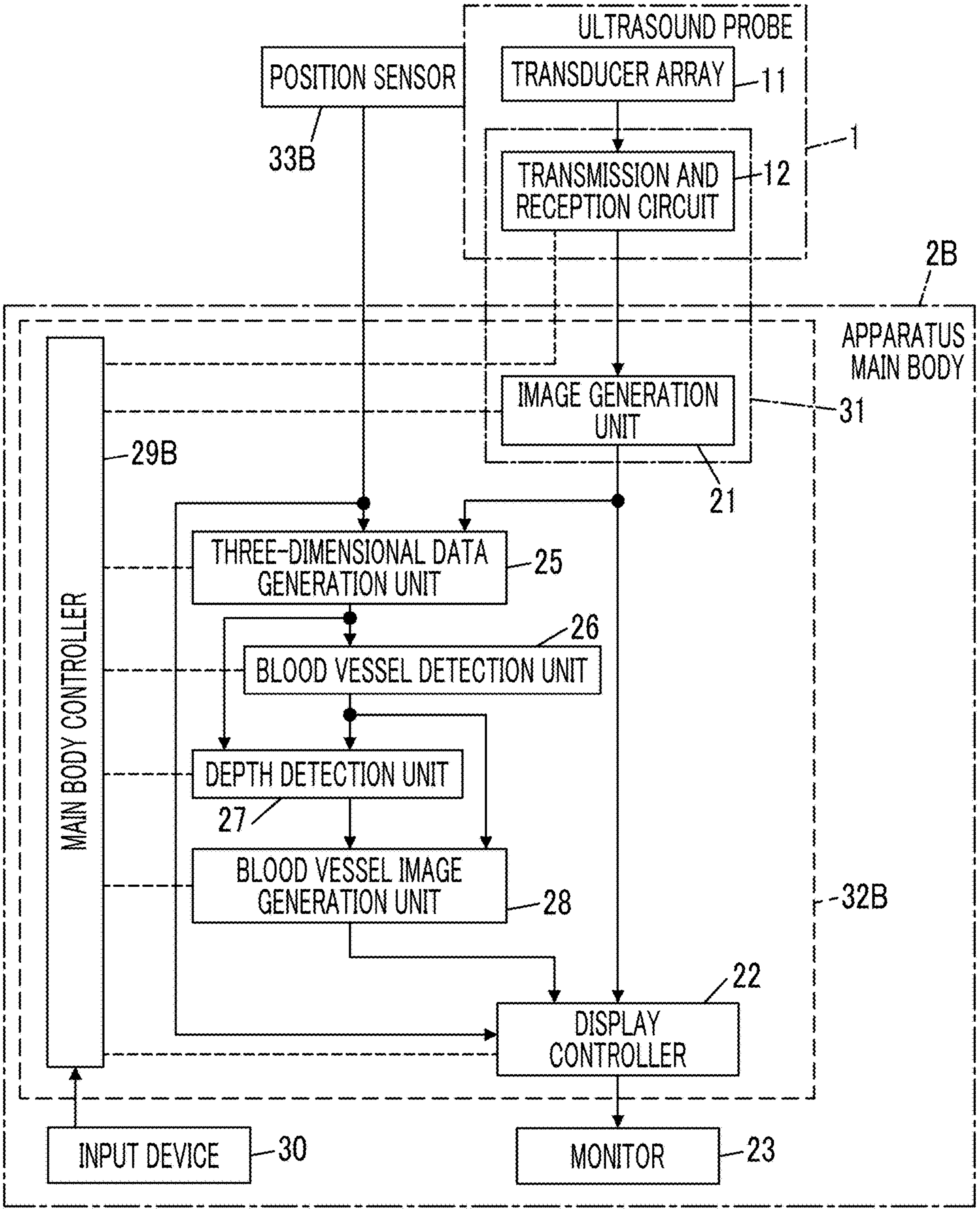
FIG. 8 is a block diagram showing a configuration of an ultrasound diagnostic apparatus according to Embodiment 2 of the present invention.

FIG. 8 shows a configuration of an ultrasound diagnostic apparatus according to Embodiment 2. The ultrasound diagnostic apparatus of Embodiment 2 comprises an apparatus main body 2B instead of the apparatus main body 2 and includes a position sensor 33B attached to the ultrasound probe 1 instead of the optical camera 3. The position sensor 33B constitutes the probe position detection unit in Embodiment 2.

The apparatus main body 2B is obtained by removing the optical image analysis unit 24 and providing a main body controller 29B instead of the main body controller 29 with respect to the apparatus main body 2 in Embodiment 1 shown in FIG. 1. In the apparatus main body 2B, the three-dimensional data generation unit 25 and the blood vessel image generation unit 28 are connected to the position sensor 33B. In addition, the image generation unit 21, the display controller 22, the three-dimensional data generation unit 25, the blood vessel detection unit 26, the depth detection unit 27, the blood vessel image generation unit 28, and the main body controller 29B constitute a processor 32B for the apparatus main body 2B.

The position sensor 33B attached to the ultrasound probe 1 is a sensor that detects the position of the ultrasound probe 1. The position sensor 33B can use, for example, a predetermined position as a reference to detect relative coordinates from the reference position as the position of the ultrasound probe 1. As the position sensor 33B, for example, a so-called magnetic sensor, an acceleration sensor, a gyro sensor, a global positioning system (GPS) sensor, a geomagnetic sensor, or the like can be used. Information on the position of the ultrasound probe 1 detected by the position sensor 33B is transmitted to the three-dimensional data generation unit 25 and the blood vessel image generation unit 28. The three-dimensional data generation unit 25 generates the three-dimensional ultrasound data of the blood vessel B of the subject based on the plurality of frames of the ultrasound images U including the minor axis image of the blood vessel B, which are acquired by the image acquisition unit 31 while performing scanning with the ultrasound probe 1 along the major axis direction D of the blood vessel B and the position of the ultrasound probe 1 detected by the position sensor 33B.

The blood vessel image generation unit 28 generates, for example, as shown in FIG. 5, a blood vessel image C depicting the blood vessel B within the subject based on the position of the ultrasound probe 1 detected by the position sensor 33B, the three-dimensional blood vessel B detected by the blood vessel detection unit 26, and the depth of the blood vessel B detected by the depth detection unit 27, and superimposes the blood vessel image C on the body surface A of the subject shown in the optical image Q captured by the optical camera which is not illustrated in FIG. 8 and displays the blood vessel image C on the monitor 23.

From the above, even in a case where the position of the ultrasound probe 1 is detected by the position sensor 33B, the blood vessel image generation unit 28 generates the blood vessel image C depicting the blood vessel B within the subject based on the position of the ultrasound probe 1 detected by the position sensor 33B, the three-dimensional blood vessel B detected by the blood vessel detection unit 26, and the depth detected by the depth detection unit 27 and displays the blood vessel image C on the monitor 23, similar to a case where the position of the ultrasound probe 1 is detected based on the optical image Q. Therefore, the user can easily grasp the position, the shape, and the depth of the blood vessel B within the subject by confirming the blood vessel image C and can easily select the puncture position in the dialysis treatment or the like.

Embodiment 3

For example, a subject undergoing a dialysis treatment undergoes frequent punctures with a thick needle in the blood vessel B, which may lead to abnormalities, such as thickening of the blood vessel wall and stenosis of the blood vessel B. Therefore, it is desirable to avoid such an abnormal location in a case of puncturing the blood vessel B of the subject with a needle. In that respect, the ultrasound diagnostic apparatus of the embodiment of the present invention can also automatically detect the abnormal location such that the user does not puncture the abnormal location.

Figure 9:
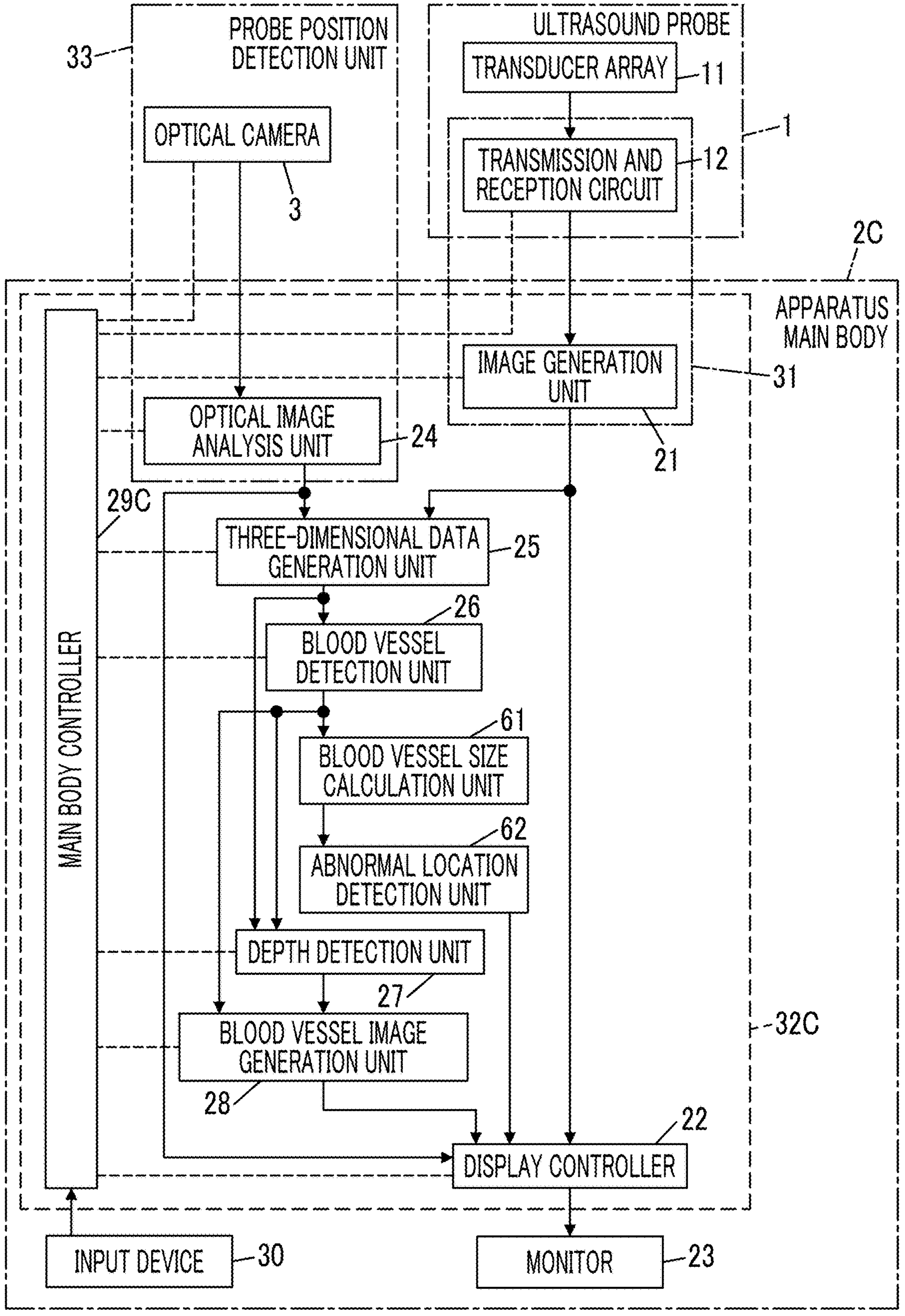
FIG. 9 is a block diagram showing a configuration of an ultrasound diagnostic apparatus according to Embodiment 3 of the present invention.

FIG. 9 shows a configuration of an ultrasound diagnostic apparatus of Embodiment 3. The ultrasound diagnostic apparatus of Embodiment 3 comprises an apparatus main body 2C instead of the apparatus main body 2 with respect to the ultrasound diagnostic apparatus of Embodiment 1 shown in FIG. 1.

The apparatus main body 2C comprises a main body controller 29C instead of the main body controller 29 and further comprises a blood vessel size calculation unit 61 and an abnormal location detection unit 62 (first abnormal location detection unit), with respect to the apparatus main body 2 in Embodiment 1. In the apparatus main body 2C, the blood vessel size calculation unit 61 is connected to the blood vessel detection unit 26 and the main body controller 29C. The abnormal location detection unit 62 is connected to the blood vessel size calculation unit 61. The abnormal location detection unit 62 is connected to the display controller 22. In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29C, the blood vessel size calculation unit 61, and the abnormal location detection unit 62 constitute a processor 32C for the apparatus main body 2C.

The blood vessel size calculation unit 61 calculates the thickness of the blood vessel wall or the diameter of the blood vessel lumen over the entire length of the blood vessel B detected by the blood vessel detection unit 26, based on the blood vessel wall and the blood vessel lumen detected by the blood vessel detection unit 26. The blood vessel size calculation unit 61 can calculate the thickness of the blood vessel wall or the diameter of the blood vessel lumen over the entire length of the blood vessel B detected by the blood vessel detection unit 26 by, for example, measuring the blood vessel wall and the blood vessel lumen of the three-dimensional blood vessel B in the plane perpendicular to the major axis direction D.

The abnormal location detection unit 62 has predetermined change rate threshold values for a spatial change rate of the thickness of the blood vessel wall in the major axis direction D and a spatial change rate of the diameter of the blood vessel lumen in the major axis direction D and detects a location where the spatial change rate of the thickness of the blood vessel wall or the diameter of the blood vessel lumen calculated by the blood vessel size calculation unit 61 exceeds the change rate threshold value.

The abnormal location detection unit 62 can calculate the spatial change rate of the thickness of the blood vessel wall in the major axis direction D by differentiating the thickness of the blood vessel wall with respect to the position of the blood vessel B in the major axis direction D in the relationship between the position of the blood vessel B in the major axis direction D and the thickness of the blood vessel wall at that position. In addition, the abnormal location detection unit 62 can calculate the spatial change rate of the diameter of the blood vessel lumen in the major axis direction D by differentiating the diameter of the blood vessel lumen with respect to the position of the blood vessel B in the major axis direction D in the relationship between the position of the blood vessel B in the major axis direction D and the diameter of the blood vessel lumen at that position.

Here, in a case where abnormalities, such as thickening of the blood vessel wall and stenosis, have occurred in the blood vessel B of the subject, the spatial change rate of the thickness of the blood vessel wall or the diameter of the blood vessel lumen rapidly increases. Therefore, a location where these spatial change rates exceed the change rate threshold values can be regarded as an abnormal location where abnormalities, such as thickening of the blood vessel wall and stenosis, have occurred.

Figure 10:
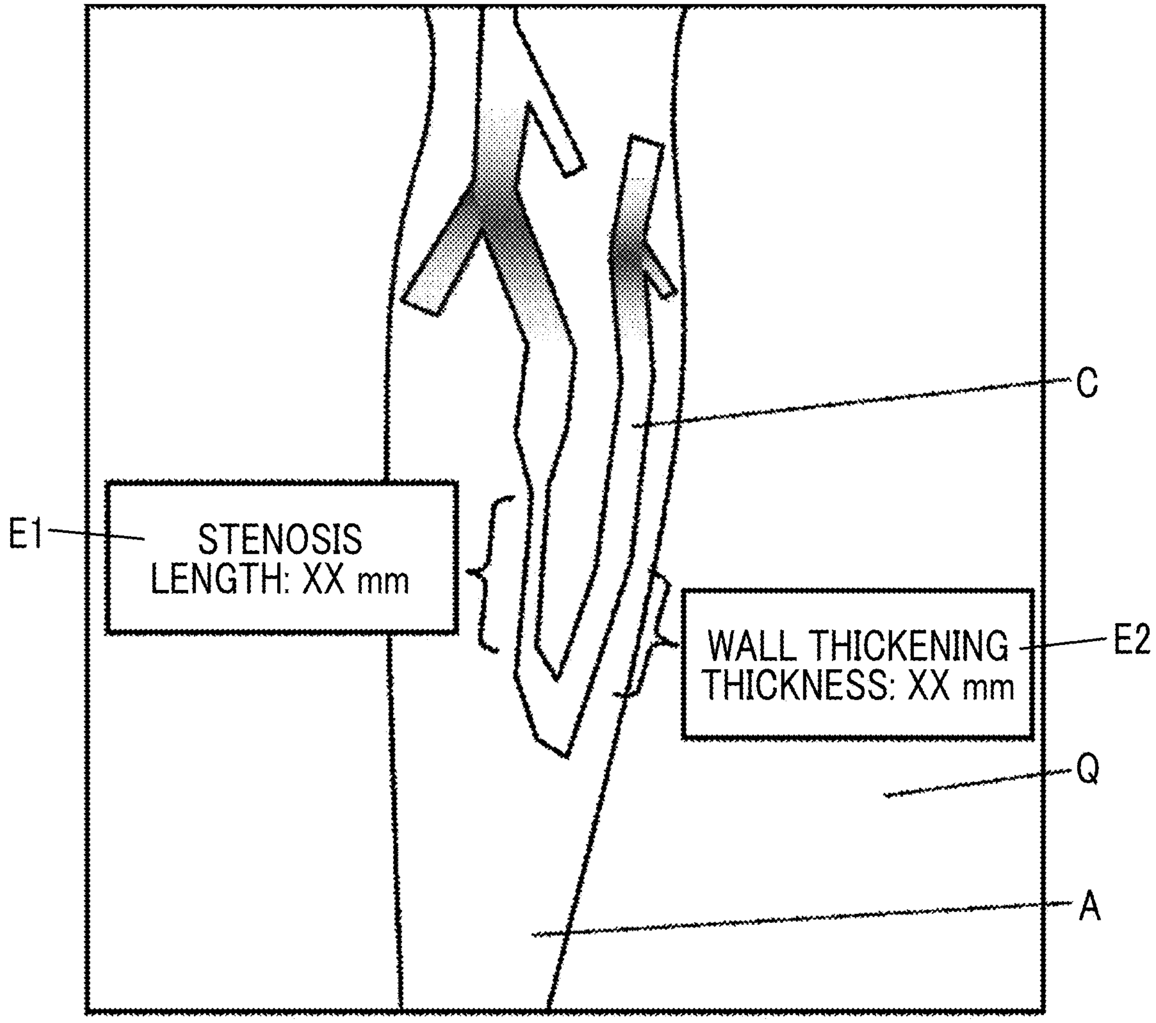
FIG. 10 is a diagram showing a display example of a location where a spatial change rate of a thickness of a blood vessel wall exceeds a change rate threshold value and a location where a spatial change rate of a diameter of a blood vessel lumen exceeds a change rate threshold value.

The abnormal location detection unit 62 displays the location where the spatial change rate of the thickness of the blood vessel wall or the diameter of the blood vessel lumen calculated by the blood vessel size calculation unit 61 exceeds the change rate threshold value, for example, as shown in FIG. 10, on the monitor 23 as the abnormal location. In FIG. 10, an example is shown in which a message E1 indicating a location where stenosis has occurred in the blood vessel B and a length thereof, such as "stenosis, length: XX mm", and a message E2 indicating a location where the blood vessel wall is thickened and a thickness thereof, such as "wall thickening, thickness: XX mm", are superimposed on the optical image Q and displayed. The user can easily grasp the position of the blood vessel B, where the needle puncture should be avoided, by confirming the display of the abnormal location and can puncture an appropriate position with the needle.

From the above, with the ultrasound diagnostic apparatus of Embodiment 3, the blood vessel size calculation unit 61 calculates the thickness of the blood vessel wall or the diameter of the blood vessel lumen over the entire length of the blood vessel B detected by the blood vessel detection unit 26, and the abnormal location detection unit 62 detects the location where the spatial change rate of the thickness of the blood vessel wall or the diameter of the blood vessel lumen calculated by the blood vessel size calculation unit 61 exceeds the change rate threshold value, and displays the location on the monitor 23. Therefore, the user can easily grasp the position of the blood vessel B, where the needle puncture should be avoided, and can easily select an appropriate position to be punctured with the needle in the blood vessel B.

The ultrasound diagnostic apparatus of Embodiment 3 has a configuration in which the blood vessel size calculation unit 61 and the abnormal location detection unit 62 are added to the ultrasound diagnostic apparatus of Embodiment 1, but a configuration may be employed in which the blood vessel size calculation unit 61 and the abnormal location detection unit 62 are added to the ultrasound diagnostic apparatus of Embodiment 2. Even in this case as well, the user can easily grasp the position of the blood vessel B, where the needle puncture should be avoided, by confirming the display of the abnormal location and can puncture an appropriate position with the needle.

Embodiment 4

The ultrasound diagnostic apparatus of the embodiment of the present invention can also display a three-dimensional image of the blood vessel B on the monitor 23 such that the user can easily determine an appropriate position to be punctured with the needle.

Figure 11:
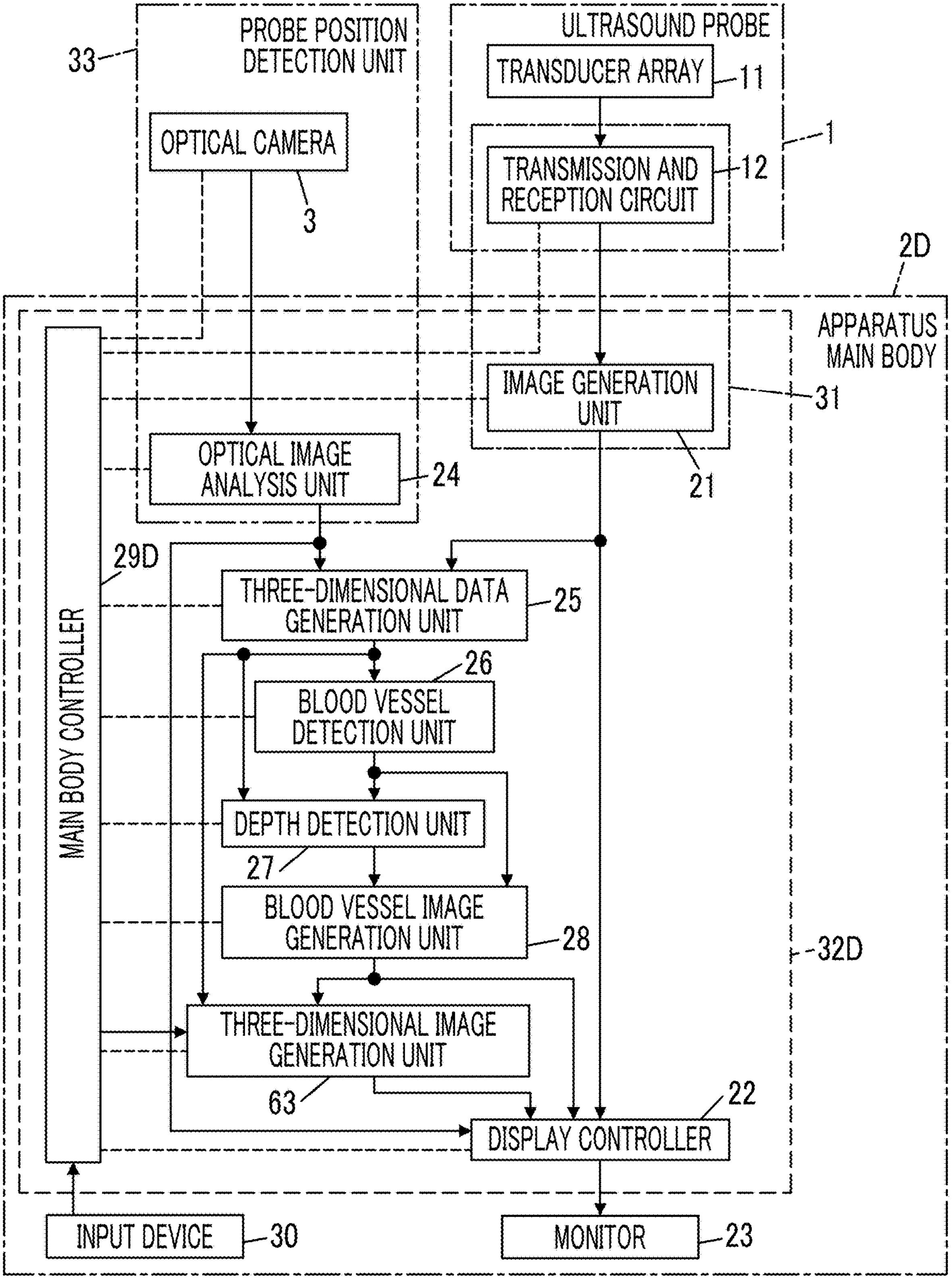
FIG. 11 is a block diagram showing a configuration of an ultrasound diagnostic apparatus according to Embodiment 4 of the present invention.

FIG. 11 shows a configuration of an ultrasound diagnostic apparatus of Embodiment 4. The ultrasound diagnostic apparatus of Embodiment 4 comprises an apparatus main body 2D instead of the apparatus main body 2 with respect to the ultrasound diagnostic apparatus of Embodiment 1 shown in FIG. 1. The apparatus main body 2D comprises a main body controller 29D instead of the main body controller 29 and further comprises a three-dimensional image generation unit 63, with respect to the apparatus main body 2 in Embodiment 1.

In the apparatus main body 2D, the three-dimensional image generation unit 63 is connected to the three-dimensional data generation unit 25, the blood vessel image generation unit 28, and the main body controller 29D. The three-dimensional image generation unit 63 is connected to the display controller 22. In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29D, and the three-dimensional image generation unit 63 constitute a processor 32D for the apparatus main body 2D.

Figure 12:
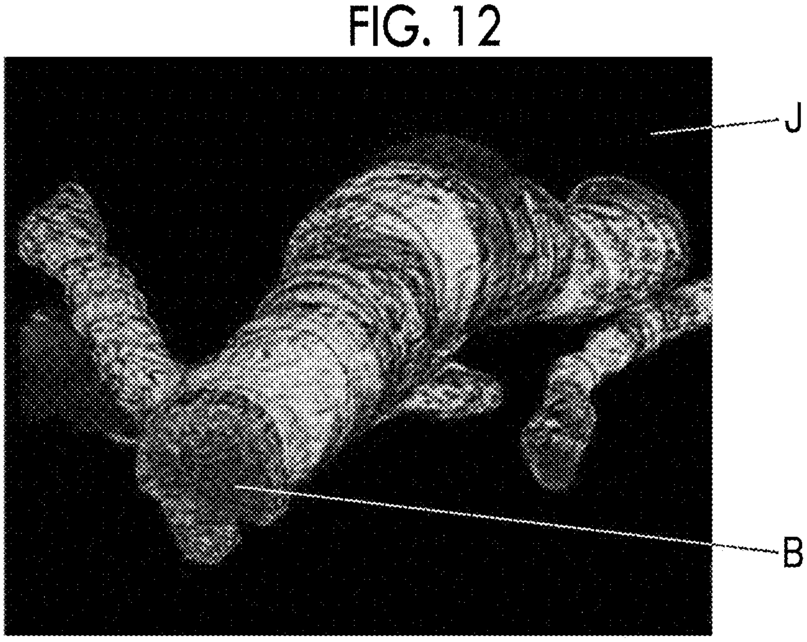
FIG. 12 is a diagram showing an example of a three-dimensional ultrasound image.

The three-dimensional image generation unit 63 generates, as shown in FIG. 12, a three-dimensional ultrasound image J corresponding to any location designated by the user via the input device 30 for the blood vessel image C from the three-dimensional ultrasound data generated by the three-dimensional data generation unit 25 and displays the three-dimensional ultrasound image J on the monitor 23. In this case, the three-dimensional image generation unit 63 can reconstruct the three-dimensional ultrasound image J of the blood vessel B such that the body surface A becomes flat in order for the user to easily grasp the change of the depth of the blood vessel B from the body surface A.

The three-dimensional image generation unit 63 can also display the three-dimensional ultrasound image J of the blood vessel B on the monitor 23 at a rotational position in accordance with a viewpoint or a rotation angle designated by the user via the input device 30.

From the above, with the ultrasound diagnostic apparatus of Embodiment 4, the three-dimensional image generation unit 63 generates, as shown in FIG. 12, the three-dimensional ultrasound image J corresponding to any location designated by the user via the input device 30 for the blood vessel image C and displays the three-dimensional ultrasound image J on the monitor 23. Therefore, the user can grasp the shape and the depth of the blood vessel B in detail and can easily select an appropriate position in the needle puncture.

The three-dimensional image generation unit 63 can also reconstruct two-dimensional images of the blood vessel B in which the blood vessel B is viewed from a plurality of directions, from the three-dimensional ultrasound data, and can display the two-dimensional image on the monitor 23 together with the three-dimensional ultrasound image J of the blood vessel B. As a result, the user can grasp the shape and the depth of the blood vessel B in more detail and can easily select an appropriate position in the needle puncture.

In addition, the ultrasound diagnostic apparatus of Embodiment 4 has a configuration in which the three-dimensional image generation unit 63 is added to the ultrasound diagnostic apparatus of Embodiment 1, but a configuration may be employed in which the three-dimensional image generation unit 63 is added to the ultrasound diagnostic apparatuses of Embodiments 2 and 3. Even in this case as well, the user can grasp the shape and the depth of the blood vessel B in detail and can easily select an appropriate position in the needle puncture.

Embodiment 5

Depending on the user's proficiency level, there may be a case where the puncture direction and the puncture angle of the needle cannot be easily decided on even though the position suitable for the needle puncture in the blood vessel B can be grasped. In that respect, the ultrasound diagnostic apparatus of the embodiment of the present invention can also automatically calculate a recommended needle puncture direction and a recommended puncture angle.

Figure 13:
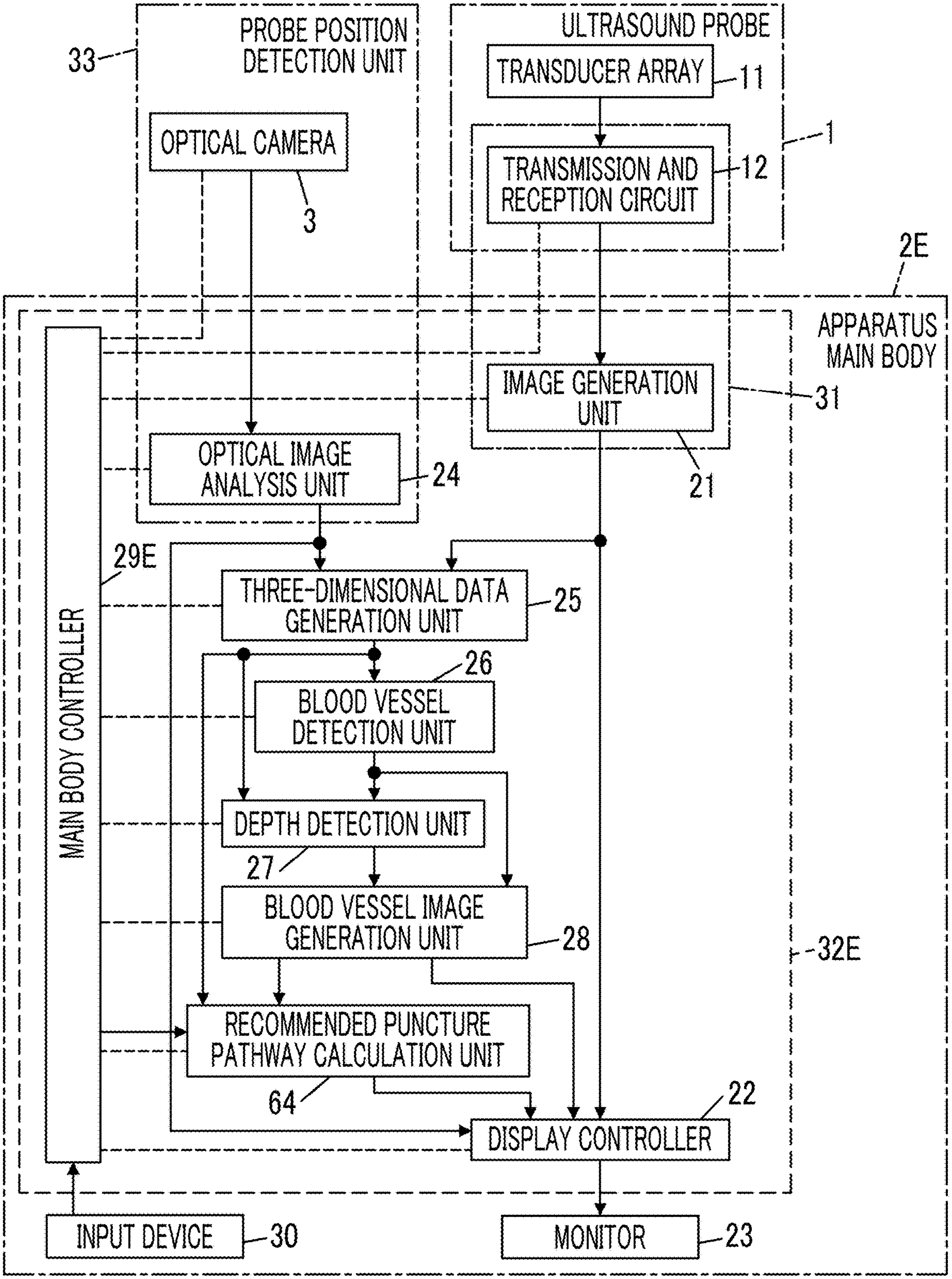
FIG. 13 is a block diagram showing a configuration of an ultrasound diagnostic apparatus according to Embodiment 5 of the present invention.

FIG. 13 shows a configuration of an ultrasound diagnostic apparatus of Embodiment 5. The ultrasound diagnostic apparatus of Embodiment 5 comprises an apparatus main body 2E instead of the apparatus main body 2 with respect to the ultrasound diagnostic apparatus of Embodiment 1 shown in FIG. 1. The apparatus main body 2E comprises a main body controller 29E instead of the main body controller 29 and further comprises a recommended puncture pathway calculation unit 64, with respect to the apparatus main body 2 in Embodiment 1.

In the apparatus main body 2E, the recommended puncture pathway calculation unit 64 is connected to the three-dimensional data generation unit 25 and the main body controller 29E. The recommended puncture pathway calculation unit 64 is connected to the display controller 22. In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29E, and the recommended puncture pathway calculation unit 64 constitute a processor 32E for the apparatus main body 2E.

Figure 14:
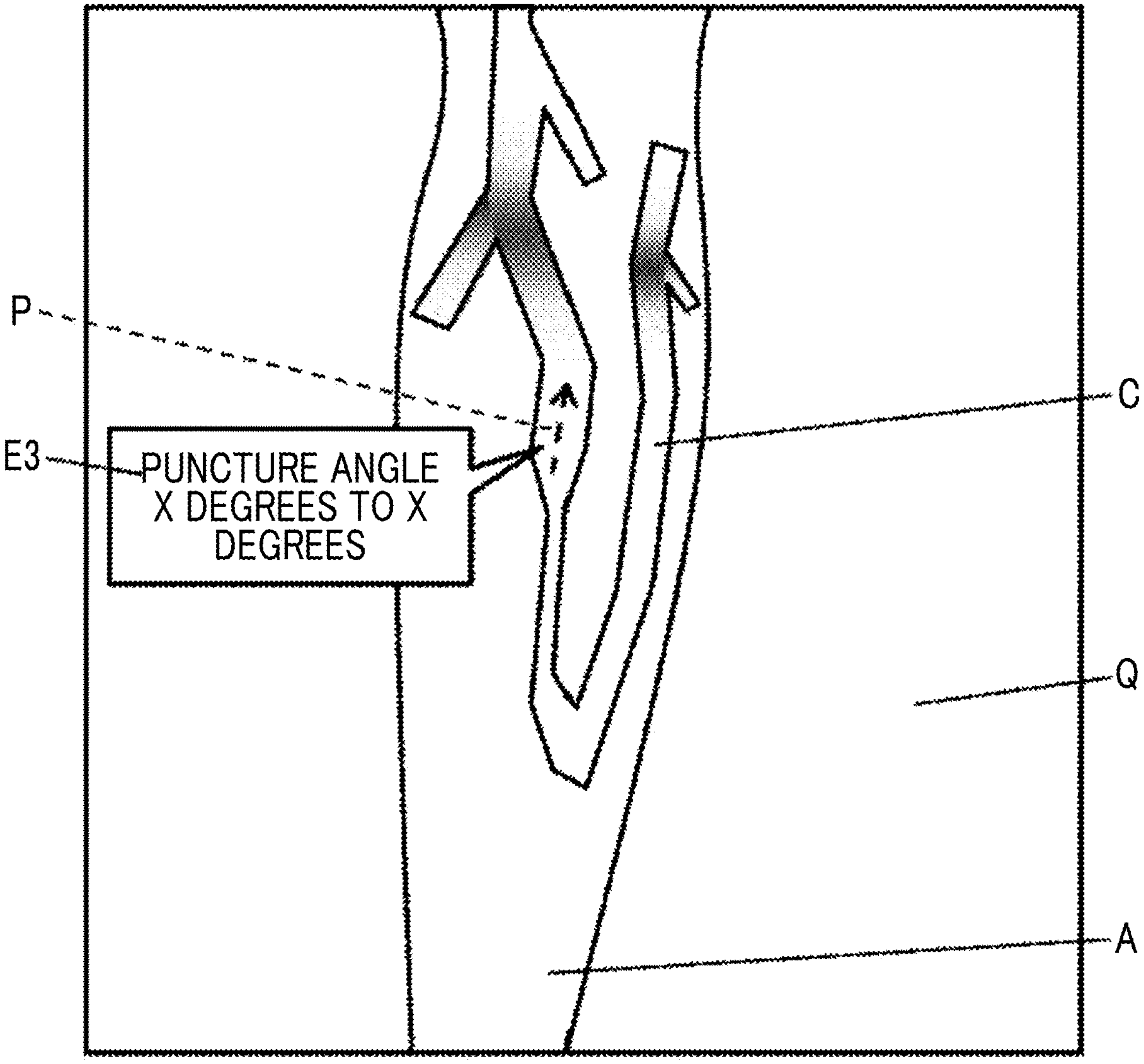
FIG. 14 is a diagram showing an example of a recommended puncture pathway.

The recommended puncture pathway calculation unit 64 calculates, for example, as shown in FIG. 14, a recommended puncture pathway including a recommended puncture direction and a recommended puncture angle with respect to the body surface A at a puncture location designated by the user via the input device 30 for the blood vessel image C from the three-dimensional ultrasound data generated by the three-dimensional data generation unit 25, and displays the recommended puncture pathway on the monitor 23. In the example of FIG. 14, as the recommended puncture pathway, an arrow P indicating the recommended puncture direction and a message E3, such as "puncture angle X degrees to X degrees", indicating the range of the recommended puncture angle with respect to the body surface A are shown.

In this case, the recommended puncture pathway calculation unit 64 can detect, for example, from the three-dimensional ultrasound data, the flow direction of the blood vessel B and the position of the abnormal location, such as the thickening of the blood vessel wall and the stenosis of the blood vessel B, in a viewpoint of viewing the body surface A of the subject from above, and can calculate, as the recommended puncture direction, a direction, which is parallel to the flow direction of the blood vessel B and has a progression direction that does not include the abnormal location, such as the thickening of the blood vessel wall and the stenosis of the blood vessel B, at the puncture location designated by the user via the input device 30 for the blood vessel image C.

In addition, the recommended puncture pathway calculation unit 64 can reconstruct, for example, a major axis image of the blood vessel B at the puncture location designated by the user via the input device 30 for the blood vessel image C from the three-dimensional ultrasound data, and can calculate, as the recommended puncture angle, a certain angle range with respect to the flow direction of the blood vessel B in the major axis image.

From the above, with the ultrasound diagnostic apparatus of Embodiment 5, the recommended puncture pathway calculation unit 64 calculates, for example, as shown in FIG. 14, the recommended puncture pathway including the recommended puncture direction and the recommended puncture angle with respect to the body surface A at the puncture location designated by the user via the input device 30 for the blood vessel image C, and displays the recommended puncture pathway on the monitor 23. Therefore, the user can easily grasp an appropriate puncture direction and an appropriate puncture angle for the decided-on puncture position by confirming the recommended puncture pathway.

The ultrasound diagnostic apparatus of Embodiment 5 has a configuration in which the recommended puncture pathway calculation unit 64 is added to the ultrasound diagnostic apparatus of Embodiment 1, but a configuration may be employed in which the recommended puncture pathway calculation unit 64 is added to the ultrasound diagnostic apparatuses of Embodiments 2 to 4. Even in this case as well, the user can easily grasp the appropriate puncture direction and the appropriate puncture angle for the decided-on puncture position by confirming the recommended puncture pathway.

Embodiment 6

An artery may be located in the vicinity of a vein within the subject. In that respect, the ultrasound diagnostic apparatus of the embodiment of the present invention can also display, for example, the vein and the artery in display forms different from each other so as to facilitate the user in avoiding the artery in the needle puncture.

Figure 15:
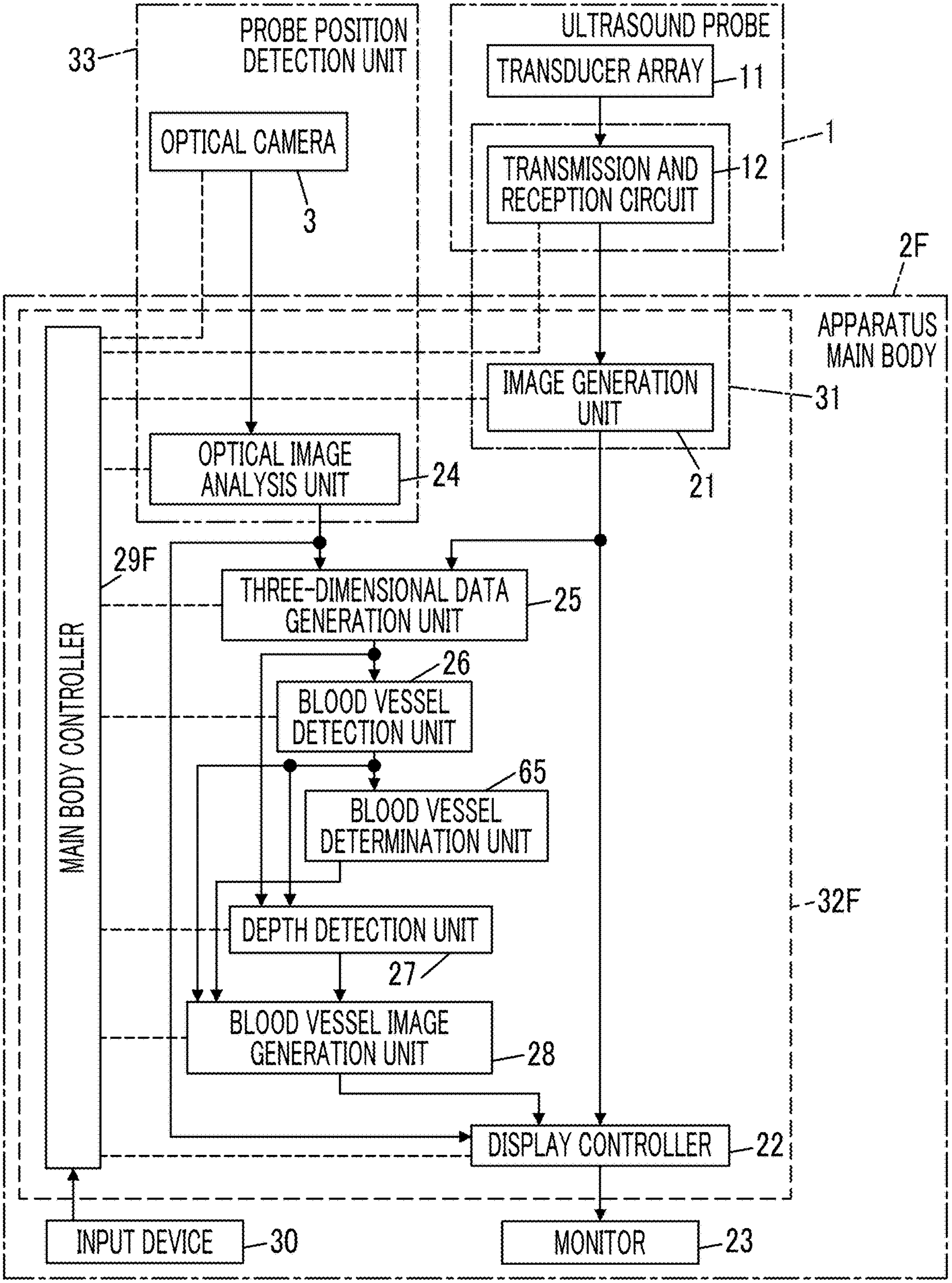
FIG. 15 is a block diagram showing a configuration of an ultrasound diagnostic apparatus according to Embodiment 6 of the present invention.

FIG. 15 shows a configuration of an ultrasound diagnostic apparatus of Embodiment 6. The ultrasound diagnostic apparatus of Embodiment 6 comprises an apparatus main body 2F instead of the apparatus main body 2 with respect to the ultrasound diagnostic apparatus of Embodiment 1 shown in FIG. 1. The apparatus main body 2F comprises a main body controller 29F instead of the main body controller 29 and further comprises a blood vessel determination unit 65, with respect to the apparatus main body 2 in Embodiment 1.

In the apparatus main body 2F, the blood vessel determination unit 65 is connected to the blood vessel detection unit 26 and the main body controller 29F. The blood vessel determination unit 65 is connected to the blood vessel image generation unit 28. In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29F, and the blood vessel determination unit 65 constitute a processor 32F for the apparatus main body 2F.

The blood vessel determination unit 65 determines whether the blood vessel B detected by the blood vessel detection unit 26 is the artery or the vein. Normally, since the artery exhibits temporal variations in blood vessel diameter due to the pulsation of the heart, the blood vessel determination unit 65 can determine the blood vessel B that exhibits temporal variations in blood vessel diameter as the artery and can determine the blood vessel B that does not exhibit temporal variations in blood vessel diameter as the vein, for example, based on the plurality of continuous frames of the ultrasound images U. The blood vessel determination unit 65 can also determine the artery and the vein using, for example, a machine learning model that has learned a large number of ultrasound images U in which arteries are captured and a large number of ultrasound images U in which veins are captured.

Figure 16:
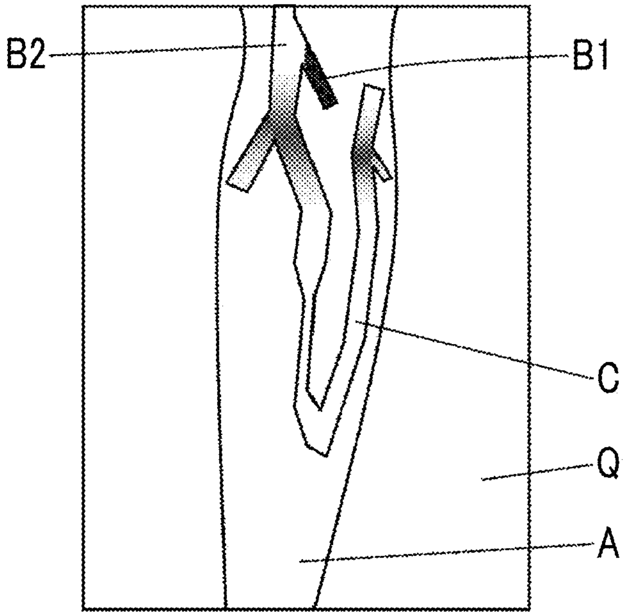
FIG. 16 is a diagram showing a display example of an artery and a vein.

The blood vessel image generation unit 28 can generate the blood vessel image C in which a depiction form of the blood vessel B is changed according to a determination result by the blood vessel determination unit 65. In this case, the blood vessel image generation unit 28 can generate the blood vessel image C in which an artery B1 and a vein B2 are depicted in colors different from each other, for example, as shown in FIG. 16. The blood vessel image generation unit 28 can also change, for example, the transparency, the brightness, or the aspects of the contour lines of the artery B1 and of the vein B2.

From the above, with the ultrasound diagnostic apparatus of Embodiment 6, the blood vessel determination unit 65 determines whether the blood vessel B detected by the blood vessel detection unit 26 is the artery B1 or the vein B2, and the blood vessel image generation unit 28 generates the blood vessel image C in which the depiction form of the blood vessel B is changed according to the determination result by the blood vessel determination unit 65. Therefore, the user can easily grasp the positions of the artery B1 and of the vein B2 by confirming the display of the monitor 23 and can easily select an appropriate puncture position in the blood vessel B.

The ultrasound diagnostic apparatus of Embodiment 6 has a configuration in which the blood vessel determination unit 65 is added to the ultrasound diagnostic apparatus of Embodiment 1, but a configuration may be employed in which the blood vessel determination unit 65 is added to the ultrasound diagnostic apparatuses of Embodiments 2 to 5. Even in this case as well, the user can easily grasp the positions of the artery B1 and the vein B2 by confirming the display of the monitor 23 and can easily select an appropriate puncture position in the blood vessel B.

Embodiment 7

A nerve bundle may be located in the vicinity of the blood vessel B within the subject. In that respect, the ultrasound diagnostic apparatus of the embodiment of the present invention can also display, for example, the nerve bundle located in the vicinity of the blood vessel B such that the risk of the needle reaching the nerve bundle can be reduced.

Figure 17:
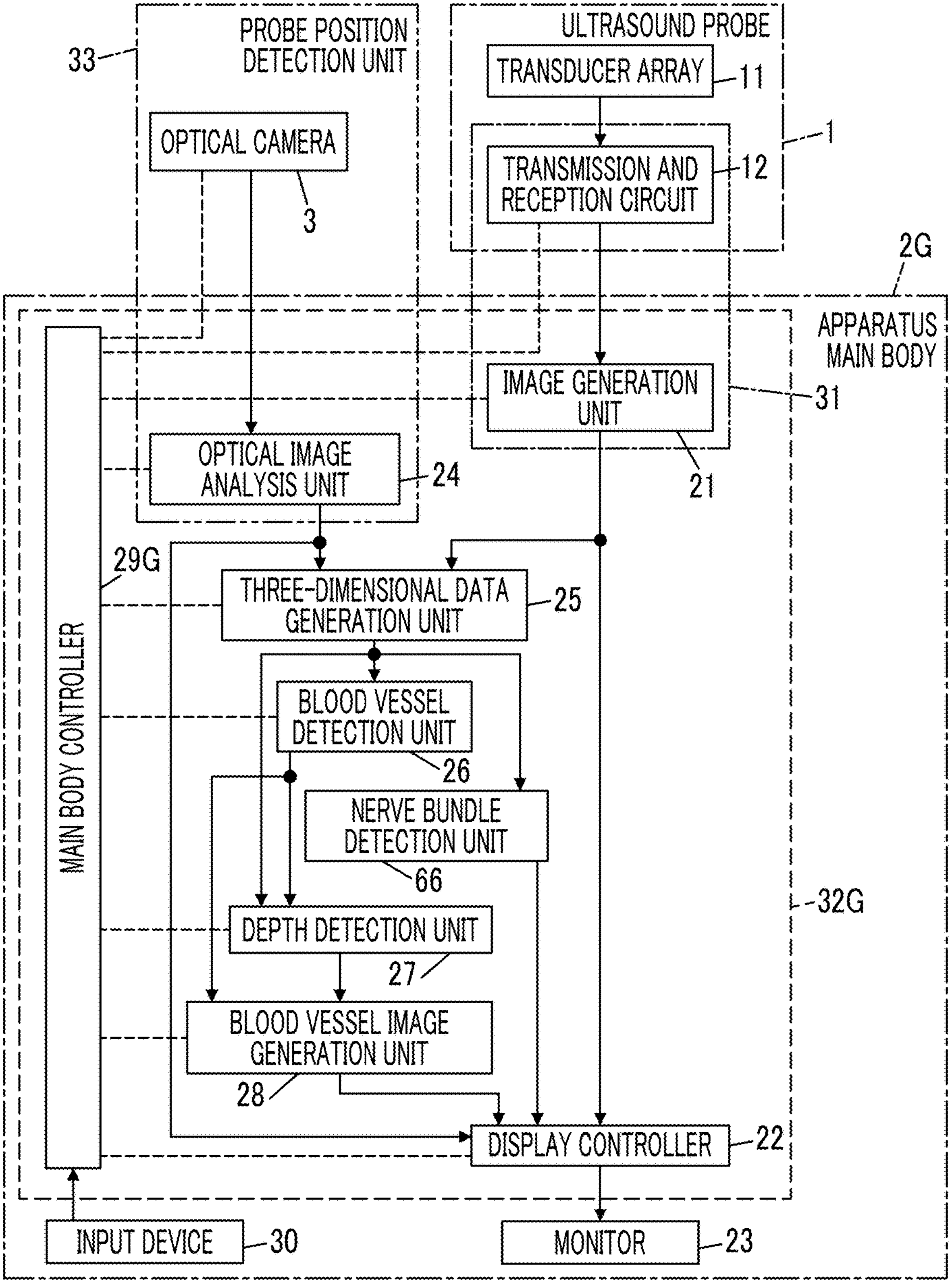
FIG. 17 is a block diagram showing a configuration of an ultrasound diagnostic apparatus according to Embodiment 7 of the present invention.

FIG. 17 shows a configuration of an ultrasound diagnostic apparatus of Embodiment 7. The ultrasound diagnostic apparatus of Embodiment 7 comprises an apparatus main body 2G instead of the apparatus main body 2 with respect to the ultrasound diagnostic apparatus of Embodiment 1 shown in FIG. 1. The apparatus main body 2G comprises a main body controller 29G instead of the main body controller 29 and further comprises a nerve bundle detection unit 66, with respect to the apparatus main body 2 in Embodiment 1.

In the apparatus main body 2G, the nerve bundle detection unit 66 is connected to the three-dimensional data generation unit 25 and the main body controller 29G. The nerve bundle detection unit 66 is connected to the display controller 22. In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29G, and the nerve bundle detection unit 66 constitute a processor 32G for the apparatus main body 2G.

Figure 18:
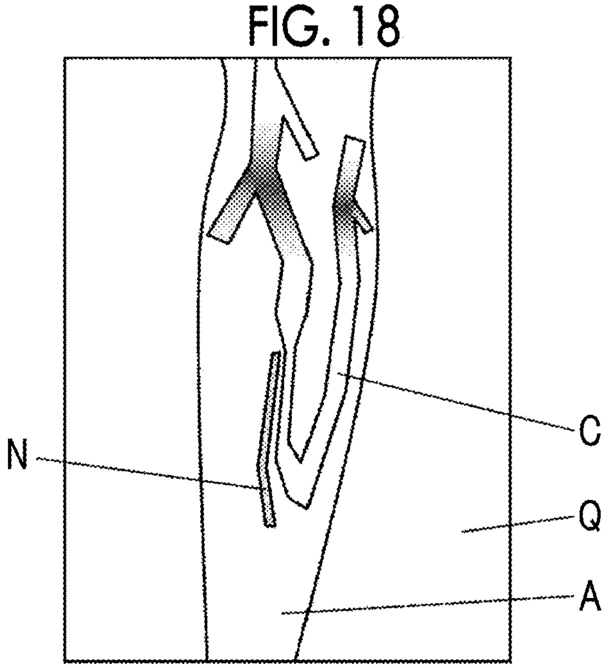
FIG. 18 is a diagram showing a display example of a nerve bundle.

The nerve bundle detection unit 66 detects the nerve bundle from the three-dimensional ultrasound data generated by the three-dimensional data generation unit 25 and displays, for example, as shown in FIG. 18, a nerve bundle N on the monitor 23 such that the nerve bundle is superimposed on the optical image Q together with the blood vessel image C. The nerve bundle detection unit 66 stores, for example, a plurality of template images representing the nerve bundles N, and can detect the nerve bundle N by searching the cross-section of the three-dimensional ultrasound data through the template matching method using the plurality of template images. The nerve bundle detection unit 66 can also detect the nerve bundle N using, for example, a machine learning model that has learned a large amount of three-dimensional ultrasound data including the nerve bundles N.

From the above, with the ultrasound diagnostic apparatus of Embodiment 7, the nerve bundle detection unit 66 detects the nerve bundle N from the three-dimensional ultrasound data generated by the three-dimensional data generation unit 25 and displays the nerve bundle N on the monitor 23. Therefore, the user can easily grasp the position of the nerve bundle N located in the vicinity of the blood vessel B and can select an appropriate puncture position in the blood vessel B so as to avoid the nerve bundle N.

The ultrasound diagnostic apparatus of Embodiment 7 has a configuration in which the nerve bundle detection unit 66 is added to the ultrasound diagnostic apparatus of Embodiment 1, but a configuration may be employed in which the nerve bundle detection unit 66 is added to the ultrasound diagnostic apparatuses of Embodiments 2 to 6. Even in this case as well, the user can easily grasp the position of the nerve bundle N located in the vicinity of the blood vessel B and can select an appropriate puncture position in the blood vessel B so as to avoid the nerve bundle N.

Embodiment 8

The ultrasound diagnostic apparatus of the embodiment of the present invention can automatically compare, for example, an observation result of the blood vessel B in a past examination with an observation result of the blood vessel B in a current examination such that the user can easily grasp the abnormal location of the blood vessel B of the subject.

Figure 19:
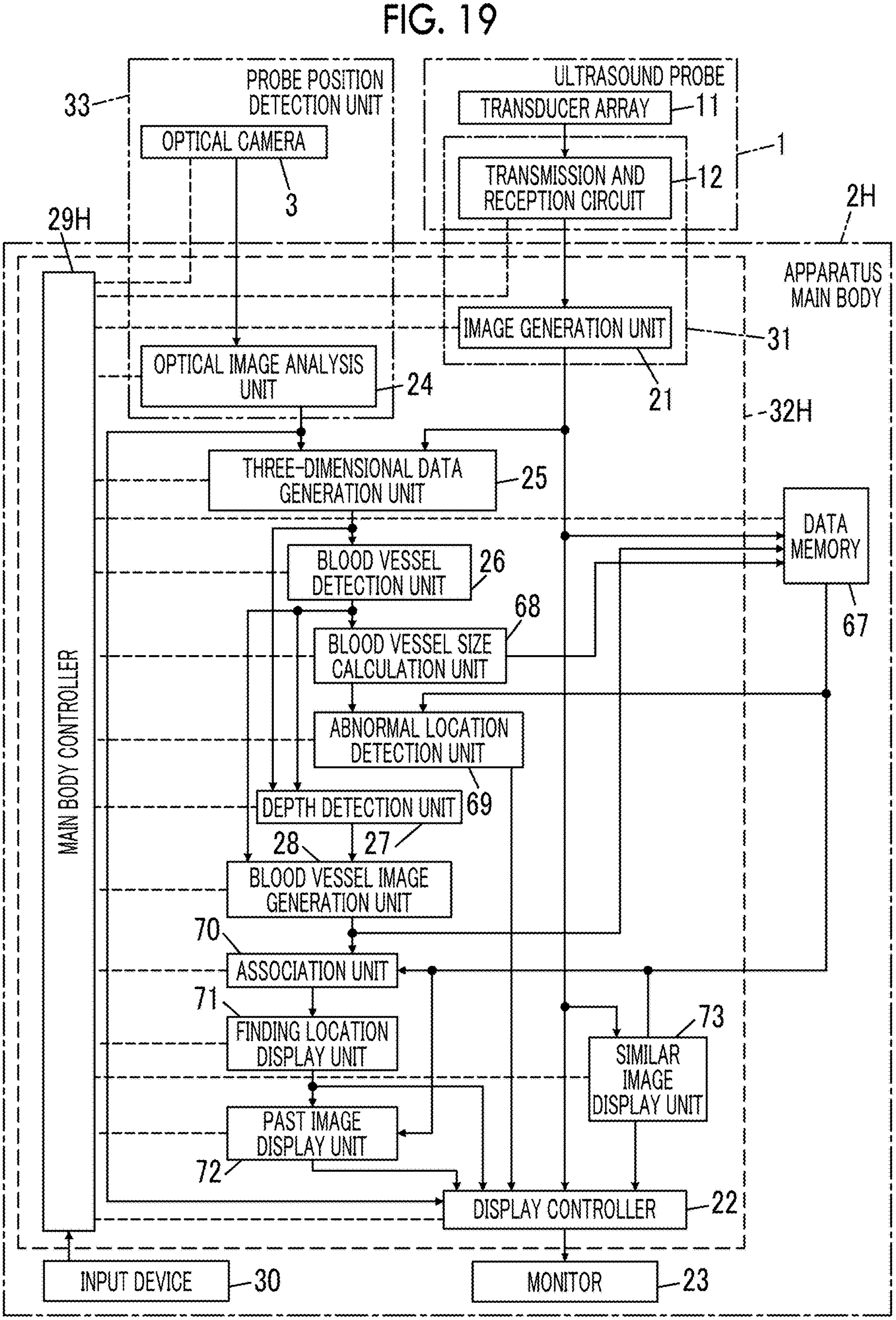
FIG. 19 is a block diagram showing a configuration of an ultrasound diagnostic apparatus according to Embodiment 8 of the present invention.

FIG. 19 shows a configuration of an ultrasound diagnostic apparatus of Embodiment 8. The ultrasound diagnostic apparatus of Embodiment 8 comprises an apparatus main body 2H instead of the apparatus main body 2 with respect to the ultrasound diagnostic apparatus of Embodiment 1. The apparatus main body 2H comprises a main body controller 29H instead of the main body controller 29 and further comprises a data memory 67, a blood vessel size calculation unit 68, an abnormal location detection unit 69 (second abnormal location detection unit), an association unit 70, a finding location display unit 71, a past image display unit 72, and a similar image display unit 73, with respect to the apparatus main body 2 in Embodiment 1.

In the apparatus main body 2H, the data memory 67 is connected to the image generation unit 21, the blood vessel image generation unit 28, and the main body controller 29H. The blood vessel size calculation unit 68 is connected to the blood vessel detection unit 26 and the main body controller 29H. The blood vessel size calculation unit 68 is connected to the data memory 67. The abnormal location detection unit 69 is connected to the data memory 67, the blood vessel size calculation unit 68, and the main body controller 29H. The abnormal location detection unit 69 is connected to the display controller 22. The association unit 70 is connected to the blood vessel image generation unit 28, the data memory 67, and the main body controller 29H. The finding location display unit 71 is connected to the association unit 70 and the main body controller 29H. The finding location display unit 71 is connected to the display controller 22. The past image display unit 72 is connected to the data memory 67, the finding location display unit 71, and the main body controller 29H. The past image display unit 72 is connected to the display controller 22. The similar image display unit 73 is connected to the image generation unit 21, the data memory 67, and the main body controller 29H. The similar image display unit 73 is connected to the display controller 22.

In addition, the image generation unit 21, the display controller 22, the optical image analysis unit 24, the three-dimensional data generation unit 25, the blood vessel detection unit 26, the depth detection unit 27, the blood vessel image generation unit 28, the main body controller 29H, the blood vessel size calculation unit 68, the abnormal location detection unit 69, the association unit 70, the finding location display unit 71, the past image display unit 72, and the similar image display unit 73 constitute a processor 32H for the apparatus main body 2H.

The blood vessel size calculation unit 68 calculates the thickness of the blood vessel wall or the diameter of the blood vessel lumen over the entire length of the blood vessel B detected by the blood vessel detection unit 26, based on the blood vessel wall and the blood vessel lumen detected by the blood vessel detection unit 26, in the same manner as in the blood vessel size calculation unit 61 in Embodiment 3.

The data memory 67 stores the ultrasound image U generated by the image generation unit 21, the thickness of the blood vessel wall or the diameter of the blood vessel lumen calculated by the blood vessel size calculation unit 68, the blood vessel image C generated by the blood vessel image generation unit 28, a finding location in the blood vessel B input in relation to the blood vessel image C by the user via the input device 30, and a finding regarding the finding location in relation to each other. The data memory 67 also stores a past ultrasound image U, a past blood vessel image C, a past finding location in the blood vessel B of the subject, and a finding content regarding the finding location.

Here, as the data memory 67, for example, recording media such as a flash memory, a hard disk drive (HDD), a solid state drive (SSD), a flexible disk (FD), a magneto-optical disk (MO disk), a magnetic tape (MT), a random access memory (RAM), a compact disc (CD), a digital versatile disc (DVD), a secure digital card (SD card), or a universal serial bus memory (USB memory) can be used.

The abnormal location detection unit 69 has a predetermined lumen diameter threshold value for a difference between a diameter of the blood vessel lumen in the past blood vessel image C, that is, a diameter of the blood vessel lumen stored in relation to the past blood vessel image C in the data memory 67, and a diameter of the blood vessel lumen in the current blood vessel image C, that is, a diameter of the blood vessel lumen calculated by the blood vessel size calculation unit 68 and related to the current blood vessel image C, and detects a location where the difference exceeds the lumen diameter threshold value.

Here, in a case where abnormalities, such as thickening of the blood vessel wall or stenosis, occur in the blood vessel B of the subject, a change in the diameter of the blood vessel lumen occurs. Therefore, at the same position of the blood vessel B, a location where the difference between the diameter of the past blood vessel lumen and the diameter of the current blood vessel lumen exceeds the lumen diameter threshold value can be regarded as the abnormal location where abnormalities, such as thickening of the blood vessel wall and stenosis, have occurred.

Figure 20:
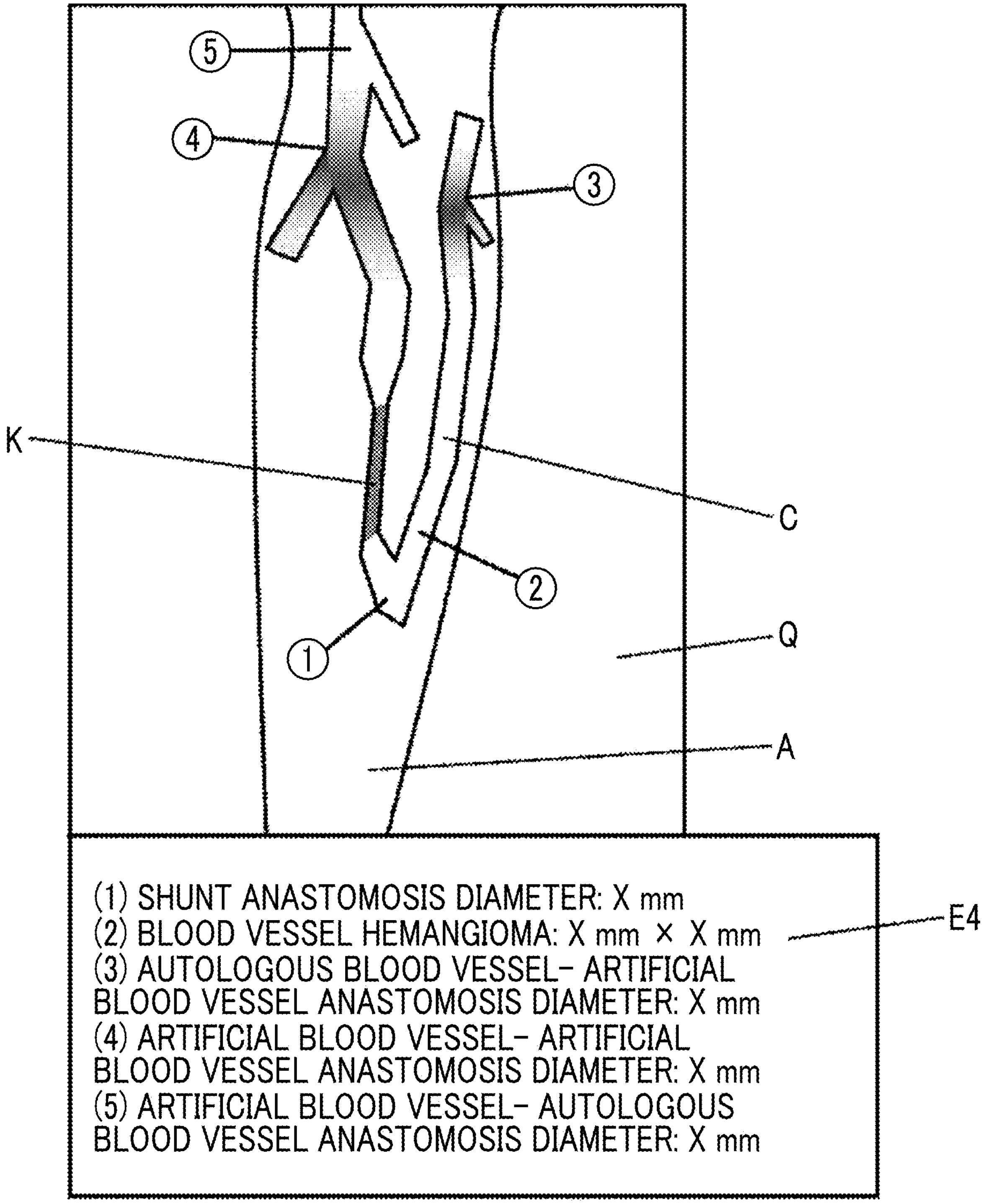
FIG. 20 is a diagram showing a display example of a current location corresponding to a past finding location and a past finding corresponding to the current location, which are superimposed on a current blood vessel image.

The abnormal location detection unit 69 can, for example, as shown in FIG. 20, highlight and display the location where the difference between the diameter of the blood vessel lumen in the past blood vessel image C and the diameter of the blood vessel lumen in the current blood vessel image C exceeds the lumen diameter threshold value as an abnormal location K on the monitor 23. The user can select an appropriate puncture position while avoiding the abnormal location K by confirming the position of the abnormal location K displayed on the monitor 23.

The association unit 70 associates the position of the past blood vessel image C stored in the data memory 67 with the position of the current blood vessel image C generated by the blood vessel image generation unit 28. In this case, the association unit 70 associates the past finding location and the past finding content, which are stored in relation to the past blood vessel image C in the data memory 67, with the current blood vessel image C together with the past blood vessel image C.

As shown in FIG. 20, for example, the finding location display unit 71 superimposes the current location associated with the past finding location on the past blood vessel image C by the association unit 70 on the current blood vessel image C and displays the current location on the monitor 23. In the example of FIG. 20, finding locations of “1” to “5” are superimposed and displayed on the current blood vessel image C.

The user can easily select an appropriate puncture position by confirming the past finding location displayed on the monitor 23 in this manner.

The past image display unit 72 displays the past finding content and the past ultrasound image U corresponding to the current location, which is displayed on the monitor 23 by the finding location display unit 71 and designated by the user via the input device 30, on the monitor 23. As shown in FIG. 20, for example, the past image display unit 72 can display the finding content corresponding to any one of the finding locations “1” to “5”, which is designated by the user, on the monitor 23 using a message E4.

The past image display unit 72 can display the past ultrasound image U corresponding to the current location designated by the user on the monitor 23 by referring to the data memory 67, but, for example, in a case where an ultrasound image U representing the major axis image or the like of the blood vessel B reconstructed based on the three-dimensional ultrasound data generated by the three-dimensional data generation unit 25 is stored in the data memory 67, the reconstructed ultrasound image U can also be displayed on the monitor 23.

The user can grasp the state of the blood vessel B of the subject in more detail by confirming the past finding content and the past ultrasound image U displayed on the monitor 23 by the past image display unit 72 and can select an appropriate puncture position.

The similar image display unit 73 refers to the data memory 67 to search the plurality of frames of the ultrasound images U acquired in the current examination for an ultrasound image U similar to the past ultrasound image U displayed by the past image display unit 72 and displays the ultrasound image U on the monitor 23. The user can use a temporal change in the past finding location in selecting an appropriate puncture position as a reference by confirming the past ultrasound image U displayed by the past image display unit 72 and the current ultrasound image U displayed by the similar image display unit 73.

From the above, with the ultrasound diagnostic apparatus of Embodiment 8, the observation result of the blood vessel B in the past examination and the observation result of the blood vessel B in the current examination are automatically compared by the abnormal location detection unit 69, the finding location display unit 71, the past image display unit 72, and the similar image display unit 73, and the result is displayed on the monitor 23. Therefore, the user can easily select an appropriate puncture position by confirming the comparison result displayed on the monitor 23.

In addition, the ultrasound diagnostic apparatus of Embodiment 8 has a configuration in which the data memory 67, the blood vessel size calculation unit 68, the abnormal location detection unit 69, the association unit 70, the finding location display unit 71, the past image display unit 72, and the similar image display unit 73 are added to the ultrasound diagnostic apparatus of Embodiment 1, but a configuration can also be employed in which the data memory 67, the blood vessel size calculation unit 68, the abnormal location detection unit 69, the association unit 70, the finding location display unit 71, the past image display unit 72, and the similar image display unit 73 are added to the ultrasound diagnostic apparatuses of Embodiments 2 and 4 to 7, and a configuration can also be employed in which the data memory 67, the association unit 70, the finding location display unit 71, the past image display unit 72, and the similar image display unit 73 are added to the ultrasound diagnostic apparatus of Embodiment 3. Even in these cases as well, the user can easily select an appropriate puncture position by confirming the comparison result displayed on the monitor 23.

EXPLANATION OF REFERENCES

1: ultrasound probe
2, 2B, 2C, 2D, 2E, 2F, 2G, 2H: apparatus main body
3: optical camera
11: transducer array
12: transmission and reception circuit
21: image generation unit
22: display controller
23: monitor
24: optical image analysis unit
25: three-dimensional data generation unit
26: blood vessel detection unit
27: depth detection unit
28: blood vessel image generation unit
29, 29B, 29C, 29D, 29E, 29F, 29G, 29H: main body controller
30: input device
31: image acquisition unit
32, 32B, 32C, 32D, 32E, 32F, 32G, 32H: processor
33: probe position detection unit
33B: position sensor
41: pulsar
42: amplification section
43: AD conversion section
44: beam former
45: signal processing section
46: DSC
47: image processing section
51: quadrature detection section
52: high-pass filter
53: fast Fourier transformation section
54: Doppler image generation section
55: complex data memory
61, 68: blood vessel size calculation unit
62, 69: abnormal location detection unit
63: three-dimensional image generation unit
64: recommended puncture pathway calculation unit
65: blood vessel determination unit
66: nerve bundle detection unit
67: data memory
70: association unit
71: finding location display unit
72: past image display unit
73: similar image display unit
A: body surface
B: blood vessel
B1: artery
B2: vein
C: blood vessel image
D: major axis direction
E1, E2, E3, E4: message
J: three-dimensional image
K: abnormal location
N: nerve bundle
P: arrow
Q: optical image
U: ultrasound image

What is claimed is:

1. An ultrasound diagnostic apparatus comprising:
an ultrasound probe;
a monitor; and
a processor configured to
detect a position of the ultrasound probe,
acquire an ultrasound image of a subject using the ultrasound probe,
generate three-dimensional ultrasound data of a blood vessel of the subject based on a plurality of frames of the ultrasound images while performing scanning with the ultrasound probe along a major axis direction of the blood vessel and the position of the ultrasound probe which is detected,
detect the blood vessel from the three-dimensional ultrasound data,
detect a depth from a body surface to the blood vessel of the subject based on the detected blood vessel,
generate a blood vessel image depicting the blood vessel within the subject based on the position of the detected ultrasound probe, the detected blood vessel, and the detected depth,
display the blood vessel image on the monitor,
associate positions of a past blood vessel image and of a current blood vessel image with each other,
display, on the monitor, a current location associated with a past finding location on the past blood vessel image while superimposing the current location on the current blood vessel image,
search a plurality of frames of ultrasound images acquired in a current examination for an ultrasound image similar to a past ultrasound image corresponding to the current location which is displayed on the monitor and designated by a user, and
display the ultrasound image on the monitor.

2. The ultrasound diagnostic apparatus according to claim 1, further comprising:
an optical camera configured to image the ultrasound probe during scanning and the subject,
wherein the processor is further configured to display the blood vessel image on the monitor while superimposing the blood vessel image on an optical image captured by the optical camera.

3. The ultrasound diagnostic apparatus according to claim 2, wherein the processor is further configured to detect the position of the ultrasound probe based on the optical image captured by the optical camera.

4. The ultrasound diagnostic apparatus according to claim 3, wherein the processor is further configured to detect a blood vessel wall and a blood vessel lumen.

5. The ultrasound diagnostic apparatus according to claim 2, wherein the processor is further configured to detect a blood vessel wall and a blood vessel lumen.

6. The ultrasound diagnostic apparatus according to claim 5, wherein the processor is further configured to detect a location where a spatial change rate of the thickness of the blood vessel wall or the diameter of the blood vessel lumen exceeds a predetermined change rate threshold value, and to display the location on the monitor.

7. The ultrasound diagnostic apparatus according to claim 1, wherein the processor is further configured to detect a blood vessel wall and a blood vessel lumen.

8. The ultrasound diagnostic apparatus according to claim 7, wherein the processor is further configured to calculate a thickness of the blood vessel wall or a diameter of the blood vessel lumen based on the blood vessel wall and the blood vessel lumen which are detected.

9. The ultrasound diagnostic apparatus according to claim 7, wherein the processor is further configured to acquire a B-mode image and a Doppler image, and detect the blood vessel lumen based on the B-mode image and the Doppler image.

10. The ultrasound diagnostic apparatus according to claim 1, wherein the processor is further configured to generate a three-dimensional ultrasound image corresponding to any location designated by a user for the blood vessel image from the three-dimensional ultrasound data, and display the three-dimensional ultrasound image on the monitor.

11. The ultrasound diagnostic apparatus according to claim 1, wherein the processor is further configured to calculate a recommended puncture pathway including a recommended puncture direction and a recommended puncture angle with respect to the body surface at a puncture location designated by a user for the blood vessel image from the three-dimensional ultrasound data, and display the recommended puncture pathway on the monitor.

12. The ultrasound diagnostic apparatus according to claim 1, wherein the processor is further configured to determine whether the detected blood vessel is an artery or a vein, and generate the blood vessel image in which a depiction form of the detected blood vessel is changed according to a determination result of whether the detected blood vessel is the artery or the vein.

13. The ultrasound diagnostic apparatus according to claim 1, wherein the processor is further configured to detect a nerve bundle from the three-dimensional ultrasound data, and display the nerve bundle which is detected on the monitor.

14. The ultrasound diagnostic apparatus according to claim 1, wherein the processor is further configured to change a display form of the blood vessel image on the monitor according to the depth which is detected.

15. A control method for an ultrasound diagnostic apparatus, comprising:

detecting a position of an ultrasound probe;

acquiring an ultrasound image of a subject using the ultrasound probe;

generating three-dimensional ultrasound data of a blood vessel of the subject based on a plurality of frames of the ultrasound images acquired while performing scanning with the ultrasound probe along a major axis direction of the blood vessel and the detected position of the ultrasound probe;

detecting the blood vessel from the generated three-dimensional ultrasound data;

detecting a depth from a body surface to the blood vessel of the subject based on the detected blood vessel;

generating a blood vessel image depicting the blood vessel within the subject based on the detected position of the ultrasound probe, the detected blood vessel, and the detected depth;

displaying the blood vessel image on a monitor;

associating positions of a past blood vessel image and of a current blood vessel image with each other;

displaying, on the monitor, a current location associated with a past finding location on the past blood vessel image while superimposing the current location on the current blood vessel image;

searching a plurality of frames of ultrasound images acquired in a current examination for an ultrasound image similar to a past ultrasound image corresponding to the current location which is displayed on the monitor and designated by a user; and displaying the ultrasound image on the monitor.

* * * * *